United States Patent
Olek et al.

(10) Patent No.: US 8,298,762 B2
(45) Date of Patent: Oct. 30, 2012

(54) SPECIFIC DNAS FOR EPIGENETIC CHARACTERISATION OF CELLS AND TISSUES

(75) Inventors: Sven Olek, Berlin (DE); Ivana Türbachova, Berlin (DE); Paul Gardina, San Francisco, CA (US)

(73) Assignee: Epiontis GmbH, Berlin (DE)

( * ) Notice: Subject to any disclaimer, the term of this patent is extended or adjusted under 35 U.S.C. 154(b) by 749 days.

(21) Appl. No.: 11/908,392

(22) PCT Filed: Mar. 13, 2006

(86) PCT No.: PCT/EP2006/002299
§ 371 (c)(1),
(2), (4) Date: Jul. 31, 2009

(87) PCT Pub. No.: WO2006/094836
PCT Pub. Date: Sep. 14, 2006

(65) Prior Publication Data
US 2009/0305234 A1    Dec. 10, 2009

(30) Foreign Application Priority Data

Mar. 11, 2005  (EP) .................................. 05005370
Jun. 6, 2005   (EP) .................................. 05012132

(51) Int. Cl.
*C12Q 1/68* (2006.01)
(52) U.S. Cl. ....................................................... 435/6.1
(58) Field of Classification Search .................. None
See application file for complete search history.

(56) References Cited

FOREIGN PATENT DOCUMENTS

| WO | WO 01/75177 A | 10/2001 |
| WO | WO 02/00928 A | 1/2002 |
| WO | WO 03/064700 A | 8/2003 |

OTHER PUBLICATIONS

Aguiar, Dean J. et al., "Gene expression in bone marrow derived mesenchymal stem cells during cartilage differentiation," *Blood*, Nov. 16, 2000, vol. 96, No. 11 Part 2, p. 113b, Abstract #4172.
Goessler, U.R. et al., "[A comparison of the gene expression patterns of human chondrocytes and chondrogen differentiated mesenchymal stem cells for tissue engineering,]" *HNO*, Apr. 2006, vol. 54, No. 4, pp. 258-266.
Imamura, T. et al., "CpG Island of Rat Sphingosine Kinase-1 Gene: Tissue-Dependent DNA Methylation Status and Multiple Alternative First Exons," *Genomics*, Academic Press, San Diego, US, Aug. 2001, vol. 76, No. 1-3, pp. 117-125.
Kawaguchi, J. et al., "The transition of cadherin expression in osteoblast differentiation from mesenchymal cells: consistent expression of cadherin-11 in osteoblast lineage," *Journal of Bone and Mineral Research: The Official Journal of the American Society for Bone and Mineral Research*, Feb. 2001, vol. 16, No. 2, pp. 260-269.
Ohgane, Jun et al., "Analysis of tissue-specific DNA methylation during development," *Methods in Molecular Biology*, Clifton, NJ, 2005, vol. 289, pp. 371-382 [Online].
Takatsu, Masaki et al., "Age-dependent alterations in mRNA level and promoter methylation of collagen alpha1(I) gene in human periodontal ligament," *Mechanisms of Ageing and Development*, Oct. 1, 1999, vol. 110, No. 1-2, pp. 37-48.
Tholpady, S. S. et al., "Mesenchymal stem cells from rat visceral fat exhibit multipotential differentiation in vitro," *Anatomical Record*, May 2003, vol. 272A, No. 1, pp. 398-402.

*Primary Examiner* — James Martinell
(74) *Attorney, Agent, or Firm* — Saliwanchik, Lloyd & Eisenschenk

(57) ABSTRACT

The present invention provides methods, nucleic acids and molecular markers for the characterization of cells, tissues and heterogeneous mixtures of cells. Specifically, it describes particular genes and genomic regions in which DNA methylation patterns are a consistent and characteristic property of different cell types, states and stages of differentiation. The invention is useful in determining the identity, composition, quality and potency of cells and cell populations. Furthermore, the invention will be useful in monitoring the differentiation of cells.

22 Claims, 2 Drawing Sheets

SPECIFIC DNAS FOR EPIGENETIC CHARACTERISATION OF CELLS AND TISSUES

FIELD OF INVENTION

The present invention provides methods, nucleic acids and molecular markers for the characterization of cells, tissues and heterogeneous mixtures of cells. Specifically, it describes particular genes and genomic regions in which DNA methylation patterns are a consistent and characteristic property of different cell types, states and stages of differentiation. The invention is useful in determining the identity, composition, quality and potency of cells and cell populations. Furthermore, the invention will be useful in monitoring the differentiation of cells. In addition, this invention allows to define discriminatory methylation profiles that are descriptive of particular cell types. Once these are known, the ratios of various cell types in a heterogeneous mixture can be determined. Due to the unpredictability of in-vitro handled cells, such a complexly informative system would be ideal as analytical tool for the determination of the quality of cell products, supplementing to, or even replacing, currently available molecular methods. Therefore, DNA methylation can provide a valuable alternative to the established analytical tools for characterising engineered cells Regenerative Medicine and Cell Identification In novel medical approaches related to "regenerative medicine" (including the sub-disciplines "tissue engineering" and "cell therapy") biological substitutes, such as cells and growth factors, are used to heal or replace damaged and diseased tissues and cells. In some cases, cells may be extensively manipulated in the laboratory and possibly changed from one cell type into another.

As one example, chondrocytes may be isolated from damaged knee cartilage, multiplied in the laboratory and re-implanted surgically to heal the injury. In other cases, such as Autologous Stem Cell Transplants (ASCT), it may be sufficient to purify or enrich a particular type of precursor cell (usually stem cells) that can develop into a target tissue naturally when re-infused into the body. ASCT, which is a widely employed treatment for blood diseases, utilises purified stem cells to rebuild the immune system after chemotherapy. More ambitious tissue engineering projects include attempts to produce pancreatic beta cells (to treat diabetes) or dopaminergic neurones (for Parkinson's and other neural diseases) from their respective precursor cells. Presently, however, extensively manipulated cells are produced mainly for metabolically inactive tissues, such as cartilage and skin.

A fundamental deficiency of regenerative medicine (and cell biology in general) is the lack of adequate methods to accurately identify and characterise living cells. Cells are complex, intrinsically variable entities whose internal workings are largely invisible to researchers. Furthermore, the engineering of cells remains at a rudimentary stage because the rules governing the conversion from one type of cell into a different type ("differentiation") are largely unknown. These difficulties are exacerbated by the long developmental times involved—usually on the order of weeks or months—and the fact that in vitro cultures are generally mixed populations of cells in various stages of differentiation or even different cell types.

Analytical shortcomings have strong adverse effects on three basic areas:

(1) Identity/purity is a confirmation that the product precisely matches its labelling and contains no extraneous material. However, because cells are complex entities that display inherent biological variation, precise definitions of cell identity (and therefore purity) with traditional technologies are dubious. Such problems are magnified by the fact that minute cellular impurities (e.g., cancerous cells) could pose immense hazards.

(2) The potency of a product is its functional ability to achieve some desired medical outcome. The intrinsic complexity and variation of cells also interferes with the ability to predict the therapeutic efficacy of product cells. Subtle, but critical, differences between any two particular batches of cells will probably not be detectable with current methods.

(3) Process optimisation requires the ability to monitor changes in cell status during in vitro manipulations to determine whether the process is proceeding in the expected direction, to analyse growth/differentiation/inhibition factors, and to optimise the process for maximum yield.

PRIOR ART

The conventional mechanisms to classify/identify cells involve extensive usage of heterogeneous biochemical and molecular procedures. These approaches, which are the current state of the art, are described below:

1. Morphology (histology): a microscopic examination of cell shape and features. This may be useful in cases in which cells display a distinctive shape (long axons in neurones) or an easily recognisable feature (a lipid vesicle stained for fats), but most cells are difficult to distinguish based on appearance alone. Histology requires a highly trained adept and is impossible to apply in high throughput.

2. Protein-based analysis (biochemical/immunological): detection of specific proteins that may be indicative of a particular cell type. The proteins are recognised by their cognate antibody either on the cell surface (immunohistology) or from disintegrated cells (immunoblotting/ELISA) (Molecular Biology Protocols (1997) ed. M. B. Frank, Oklahoma City, USA; Current Protocols in Molecular Biology (2001) ed. F. M. Ausubel et al., John Wiley & Sons, NY, USA, 2001). These assays are generally sensitive, fast and simple, and offer the possibility of cell sorting with fluorescently or magnetically tagged antibodies. However, they provide little informational complexity since each antibody recognises only one particular protein. This is a major disadvantage since a single protein marker is rarely a guarantee of a particular cell type. Larger scale protein detection methods (proteomics) suffer from insufficient sensitivity and a lack of capability for automation.

3. RNA-based analysis: detection of mRNA, which reflects gene expression, is performed in individual analyses or in array systems (Spellman et al., Mol Biol Cell 9:3273-97, 1998; DeRisi et al., Science 278:680-686, 1997; Burton et al., Gene 293:21-31 2002). This widely used technology can produce a great deal of information about the current state of the cell since the overall pattern of gene expression is revealed. Aside from its technologically difficult set-up, the decisive drawback of this system is the instability of RNA. Every experiment with RNA must take into account the degradation of RNA that may occur during sample collection, storage and the experimental procedure. This is particularly problematic when working with archived samples (e.g., preserved biopsies) or with limiting amounts of cellular material. A further, biologically inherent problem is that mRNA fluctuates in response to temporary changes environmental conditions. Together, these factors mean that meaningful expression changes are blurred by random degradation and transient background noise. Robustness, reproducibility and interpretation are therefore a grave issues for all RNA-based technologies. Both biological and stochastic variability must be countered by intense bioinformatic analysis. In general, RNA-based arrays are a useful discovery tool, but not yet widely applicable as a clinical or large scale assay method (Miller et al., Cancer Cell 2:353-61, 2002; Nadon and Shoemaker, Trends Genet 18:265-71, 2002; Murphy D, Adv Physiol Educ, 26:256-70, 2002).

DNA Methylation

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long term identity of various cell types.

The primary target of methylation is the two nucleotide sequence Cytosine-Guanine (a 'CpG site'); within this context cytosine (C) can undergo a simple chemical modification to become 5-methyl-cytosine. In the human genome, the CG sequence is much rarer than expected except in certain relatively dense clusters called 'CpG islands'. CpG islands are frequently associated with gene promoters, and it has been estimated that over half of human genes have CpG islands (Antequera and Bird, Proc Natl Acad Sci USA. 90:11995-9, 1993).

Aberrant methylation of DNA frequently accompanies the transformation from healthy to cancerous cells. Among the observed effects are genome-wide hypomethylation, increased methylation of tumour suppressor genes and hypomethylation of many oncogenes (reviewed by Jones and Laird, Nature Genetics 21:163-167, 1999; Esteller, Oncogene 21:5427-5440, 2002; Laird, Nature Reviews/Cancer 3:253-266, 2003). Methylation profiles have been recognised to be tumour specific (i.e., changes in the methylation pattern of particular genes or even individual CpGs are diagnostic of particular tumour types) and there is now an extensive collection of diagnostic markers for bladder, breast, colon, oesophagus, stomach, liver, lung, and prostate cancers (summarised by Laird, Nature Reviews/Cancer 3:253-266, 2003).

Epigenetic control by methylation is essential for early development including embryogenesis, X-chromosome inactivation and imprinting (monoallelic silencing) of either the paternal or maternal allele (Erlich, J Cellular Chem 88:899-910, 2003). There is also a class of genes that is active in the germline, but is silenced by methylation in somatic cells (Bird, Genes and Dev 16:6-21, 2002; Li, Nature Reviews/Genetics 3:662-673, 2002).

Tissue-specific methylation also serves in regulating adult cell types/stages, and there are examples in which a causal relationship between methylation and gene expression has been established. The following is a partial list of genes for which methylation changes are strongly implicated in controlling gene expression in tissue-specific manner: Lactate dehydrogenase C (testes); Oxytocin receptor (blood & liver); Tyrosine aminotransferase (liver); GFAP (astrocytes); and Leukosialin (leukocytes). In other cases, methylation may be a byproduct of some other primary regulation, or it is required to lock the gene in the 'off' state (Erlich, J Cellular Chem 88:899-910, 2003). However, for a statistical correlation between methylation patterns and cell types, the recognition of a causal relationship is not required.

A previously published example for such a cell type and cell status specific modification of certain gene regions is found during the lineage commitment of T-cells to helper T-cells (Th1 or Th2). Naïve (unstimulated) CD4+ T-cells become activated upon encountering an antigen and can be committed to alternative cell fates through further stimulation by interleukins. The two types of helper T-cells show reciprocal patterns of gene expression; Th1 produces Interferon-gamma (IFN-g) and silences IL-4, while Th2 produces IL-4 and silences INF-g (Ansel et al., Nature Immunol 4:616-623, 2003). For both alternative cell fates, the expression of these genes is inversely correlated with methylation of proximal CpG sites. In Th2 and naïve T-cells the IFN-g promoter is methylated, but not in Th1 cells where IFN-g is expressed (Attwood et al., CMLS 59:241-257, 2002). Conversely, the entire transcribed region of IL-4 becomes demethylated under Th2-inducing conditions, which strongly correlates with efficient transcription of IL-4. In Th1 cells, this extensive demethylation does not occur, rather particular untranscribed regions gradually become heavily methylated and IL-4 is not expressed (Lee et al., Immunity 16:649-660, 2002). Furthermore, Bruniquel and Schwartz (Nat Immunol. 4:235-40, 2003) have demonstrated that in naïve T-cells, the IL-2 promoter is heavily methylated and inactive, but after activation of the naïve T-cell, the IL-2 gene undergoes rapid and specific demethylation at 6 consecutive CpGs. This alteration in methylation patterns occurs concomitantly with cell differentiation and increased production of the IL-2 product.

Previous suggestions to use genomic methylation patterns as discriminatory tools in cell typing (Ataru, et al., EP 1 213 360, JP 2002-171973) rely mainly on what are in fact "discovery" methods. These are broad screening techniques for uncovering localised differences in the methylation patterns between two or more pure samples of cells. However, further steps are required to determine which exact DNA regions are affected by differential methylation. An effective analytical tool must be guided by specific markers—known targets whose methylation status is an absolute indicator of the cell type. Such large scale discovery methods are not useful as an assay method since:

1. they are not useful in quantitating the proportions of mixed cell populations;
2. they are not capable of detecting minute impurities (e.g., cancerous cells);
3. they are not applicable as a routine testing mechanism or as a large scale, high throughput assay technology; and
4. usable markers must be identified and validated on multiple samples to establish a true statistical significance.

It is therefore an object of the present invention, to provide a method of expression analysis and, in particular, expression analysis based on DNA methylation analysis as a superior tool that can supplement or replace conventional methodologies as an indicator of cell type and status.

This object of the present invention, in one aspect thereof, is solved by a method for determining the presence of a cell in a biological sample, comprising the step of determining the expression level of at least one of the genes selected from the group of COL3A1, CAV1, PRELP, SPP1, CHAD, ANXA6, KRTHB6, BGN, LTA, FGFR1, HIF1A, GDF5, PTHR1, BMP4, GLI3, COL2A1, IGF2, LPIN1, TDGF1, KRT8, CD4, CNTN1, COL6A3, FMOD, PKNOX2, C15orf27, ROPN1L, and ACVRL1, whereby an expression profile is generated that is specific for the cellular characteristics of a selected cell.

Thus, in one aspect thereof, the present invention refers to specific genes whose expression was surprisingly found to be indicative for certain cell types and statuses. In one aspect of the present invention, these genes can therefore be used to characterise cell types and statuses in biological samples that contain a mixture of, for example, cells of unknown type and/or status.

Preferred is a method according to the present invention, wherein the expression level of at least two of said genes is determined. Preferred is further a method according to the present invention, wherein the expression level of all of said genes is determined. The genes that form the basis of the present invention are preferably to be used to form a "gene panel", i.e. a collection comprising the particular genetic sequences of the present invention and/or their respective informative expression and/or methylation sites. The formation of gene panels allows for a quick and specific analysis which is indicative for particular cell types and statuses. The gene panel(s) as described and employed in this invention can be used with surprisingly high efficiency for the determination of the presence of a cell in a biological sample. In addition, the use of multiple CpG sites from a diverse array of genes allows for a high degree of sensitivity and specificity in comparison to single gene diagnostic and detection tools.

In another aspect thereof, the method according to the present invention further comprises a specific selection of the genes to be determined based on the quality of the expression analysis for said selected cell. This is, while the broad panel with 25 genes can be employed for distinguishing a wide range of cell types with highest accuracy, it is possible to using only a fraction of the panel for the identification and quantification of a smaller group of cell types. In cases where it is known that not all cell types may be present or relevant for the analysis, a selected panel consisting of less markers than all 25 may be used. For example, in a case where a differentiation experiment is performed with mesenchymal stem cells that produces only a subset of cell types within the mesengenic differentiation pathway (e.g., adipocytes, chondrocytes, fibroblasts and osteoblasts), there is demand only for the analysis of 5 cell types and their differential methylation patterns. For this analysis, one may therefore only include markers for mesenchymal stem cells, adipocytes, chondrocytes, fibroblasts and osteoblasts, while one may not be looking for markers for keratinocytes or melanocytes. In this case, a mini-marker panel may be generated for this purpose, with less than the full set of 25 markers to achieve both identification and quantification of the investigated population. In the most extreme case, such minipanel may—in dependence on the addressed question—consist of no more than one marker. This minimal scenario is feasible in two situations. On one hand such situation could occur when only two cell types are possibly present in a heterogeneous cell population. In this case, a single marker gene that has a consistent and distinctive methylation pattern between the two cell types is capable of distinguishing and quantifying them. Alternatively, such minimal panel is applicable in a more heterogeneous mixture (i.e. more than two cell types are possibly present), when the single investigated marker is known to be exclusively methylated (or unmethylated) in one particular cell type, while it is in the opposite state in all other cells. In this latter case and when the addressed question only refers to the quantification and analysis of the presence of this particular one cell type, a single marker from the large panel is eligible.

It is also an alternative embodiment of the invention to base the determination of the presence of a cell type in a biological sample on a combination of different markers as described above. To increase the likelihood of a correct determination, it is preferred that the expression of several selected additional genes is investigated. It is preferred that in such a "mini panel" comprising one or more genes, additional genes are used up to a number of 25. The preferred number of genes to be added to such a mini panel, would be one or more out of the group as described above. Especially preferred would be a combined analysis of up to 8 of the 25 genes as described, in order to distinguish between cell types and statuses with a sufficient high level of quality of said analysis. Other preferred combination would comprise the expression analysis of 4, 5, 6 and 7 genes. Wherever in the following the invention is described specifically for a particular cell type that is detected, it is meant to also include a combination of one gene of the above panel with one or more of the named genes.

While all of the present markers carry useful information in various contexts, there are several preferred combinations with variable utility. For example, COL6A3, FMOD, COL3A1, GDF5, and HIF1A typically show large blocks of consecutive CpGs which are either strongly methylated or strongly unmethylated in many cell types. Because of their 'all-or-none' character, these markers are likely to be very consistent and easy to interpret for many cell types. Thus, especially preferred would be a combined analysis of these 5 markers—or if an equivalent accuracy is achieved, possibly a subset of these markers consisting of 4, 3 or even 2 markers. Markers/CpGs that are consistently, e.g., 30% methylated in one cell type and 70% methylated in another cell type are also very useful. In some cases, the discriminatory methylation may be restricted to one or a few CpGs within the gene, but individual CpGs can be reliably assayed, as with single base extension (see below).

Certain markers demonstrated methylation patterns affecting regions of specific genes that were particularly distinctive in some cell types relative to the other cell types tested. For example, regions of CHAD, COL2A1, CAV1, ACVRL1 and ANXA6 are most heavily methylated in melanocytes, while PTHR1, KRT9 and FGFR1 are most heavily methylated in keratinocytes. Genes FMOD, FGFR1, HIF1A and CNTN1 are least methylated in chondrocytes, COL3A1 is least methylated in adipocytes, KRT8 and CAV1 are least methylated in keratinocytes, KRT9 the least in melanocytes, and CD4 the least in Mesenchymal Stem Cells (MSCs). Keratinocytes and melanocytes are methylated in PTHR1 and COL6A3, while all the other cell types were not. Gene SPP1 is distinctive for osteoblasts among the differentiated cell types tested. Heavy methylation in GDF5 separates keratinocytes and melanocytes from all other cell types except osteoblasts (which is weakly methylated). CAV1 appears most useful in separating melanocytes from keratinocytes, while BGN appears most useful in separating melanocytes from fibroblasts, and FGFR1 for separating chondrocytes from keratinocytes. Thus, other preferred combinations would comprise the expression analysis of 2, 3, 4, 5 or 6 genes. The genes FMOD, FGFR1, HIF1A, KRT8, PKNOX2, ROPN1L, and C15orf27 can be used in order to distinguish between chondrocytes and synovial fibroblasts/fibroblasts.

Also, some CpGs in particular genes (FGFR1, HIF1A, BGN, CHAD, GLI3 and CD4) appear to be sensitive to changes in growth conditions (e.g., prolonged growth as a monolayer), while some (CHAD, ANXA6, BGN, HIF1A and PRELP) are sensitive to induction with growth factors.

Preferred is a method according to the present invention, wherein determining the expression level comprises determining the mRNA and/or protein expression and/or analysis of the methylation status and/or analysis of other epigenetic markers.

Said expression level analysis of the genes may be enabled by means of mRNA expression analysis or protein expression analysis or by analysis of its genetic modifications leading to an altered expression. However, in the most preferred embodiment of the invention, the expression analysis is enabled by means of analysis of the methylation status of CpG sites within the genes (e.g. in introns and/or exons), and/or their promoter or regulatory elements, and/or contiguous regions.

To detect the levels of mRNA encoding the genes in a detection system, a sample is obtained from a patient. Said obtaining of a sample is not meant to be retrieving of a sample, as in performing a biopsy, but rather directed to the availability of an isolated biological material representing a specific tissue, relevant for the intended use. The sample can be—amongst other as described herein below—primary cell cultures, cell lines, differentiated cells, a surgically removed tissue sample, a biopsy sample as taken by a surgeon and provided to the analyst or a sample of blood, plasma, serum or the like. The sample may be treated to extract the nucleic acids contained therein. The resulting nucleic acid from the sample is subjected to gel electrophoresis or other separation techniques. Detection involves contacting the nucleic acids and in particular the mRNA of the sample with a DNA sequence serving as a probe to form hybrid duplexes. The stringency of hybridisation is determined by a number of factors during hybridisation and during the washing procedure, including temperature, ionic strength, length of time and concentration of formamide. Detection of the resulting duplex is usually accomplished by the use of labelled probes. Alternatively, the probe may be unlabeled, but may be detectable by specific binding with a ligand which is labelled, either directly or indirectly. Suitable labels and methods for labelling probes and ligands are known in the art, and include, for example, radioactive labels which may be incorporated by known methods (e.g., nick translation or kinasing), biotin, fluorescent groups, chemiluminescent groups (e.g., dioxetanes, particularly triggered dioxetanes), enzymes, antibodies, and the like.

In order to increase the sensitivity of the detection in a sample of mRNA encoding the genes, the technique of reverse transcription/polymerisation chain reaction can be used to amplify cDNA transcribed from mRNA encoding the genes. The method of reverse transcription/PCR is well known in the art. The reverse transcription/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and gene specific primers. (Belyavsky et al, Nucl Acid Res 17:2919-2932, 1989; Krug and Berger, Methods in Enzymology, Academic Press, N.Y., Vol. 152, pp. 316-325, 1987 which are incorporated by reference in their entireties).

The present invention may also be described in certain embodiments as a kit for use in determining the presence of a cell in a biological sample through testing of a biological sample. A representative kit may comprise one or more nucleic acid segments as described above that selectively hybridise to the mRNA of at least one of the above genes and a container for each of the one or more nucleic acid segments. In certain embodiments the nucleic acid segments may be combined in a single tube. In further embodiments, the nucleic acid segments may also include a pair of primers for amplifying the target mRNA. Such kits may also include any buffers, solutions, solvents, enzymes, nucleotides, or other components for hybridisation, amplification or detection reactions. Preferred kit components include reagents for reverse transcription-PCR, in situ hybridisation, Northern analysis and/or restriction polymorphism analysis (RPA).

The present invention further provides for methods to detect the presence of the polypeptide of the genes as above, e.g., in a sample obtained from a subject. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see Basic and Clinical Immunology, Sites and Terr, eds., Appleton & Lange, Norwalk, Conn. pp 217-262, 1991 which is incorporated herein by reference). Preferred are binder-ligand immunoassay methods including reacting antibodies with an epitope or epitopes of the genes and competitively displacing a labelled protein or derivative thereof.

Certain embodiments of the present invention comprise the use of antibodies specific to the polypeptide encoded by the genes as above. In certain embodiments production of monoclonal or polyclonal antibodies can be induced by the use of the polypeptide(s) of the gene as antigen(s). Such antibodies may in turn be used to detect expressed proteins as markers for detecting the presence of the polypeptide of the genes as above. The levels of such proteins present in the peripheral blood of a patient may be quantified by conventional methods. Antibody-protein binding may be detected and quantified by a variety of means known in the art, such as labelling with fluorescent or radioactive ligands. The invention further comprises kits for performing the above-mentioned procedures, wherein such kits contain antibodies specific for the polypeptides of the genes as above.

Numerous competitive and non-competitive protein binding immunoassays are well known in the art. Antibodies employed in such assays may be unlabeled, for example as used in agglutination tests, or labelled for use a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like. Polyclonal or monoclonal antibodies to the genes as above or an epitope thereof can be made for use in immunoassays by any of a number of methods known in the art. One approach for preparing antibodies to a protein is the selection and preparation of an amino acid sequence of all or part of the protein, chemically synthesising the sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference). Methods for preparation of the polypeptides of the genes as above or an epitope thereof include, but are not limited to chemical synthesis, recombinant DNA techniques or isolation from biological samples.

In the context of the present invention, it could be shown that promoters, promoter-proximal regions or coding sequences of particular genes show cell type- or state-specific chemical modifications. The inventors revealed genes and gene regions that behave principally similar to the example stated above for T cell differentiation. In particular, a number of genes/gene regions have been discovered that are sensitive indicators of cell type/status depending on their degree of methylation. The methylation phenotype of these regions are found to be variable between cell types, but maintain a consistent methylation phenotype within cell types. They have been validated on multiple samples of each cell type and will serve as markers that can be specifically targeted in assays to determine cell identity, purity and potency. Furthermore, they are indicators of essential changes in cellular character and thus are useful in tissue engineering and for monitoring compounds that effect such changes.

Thus, in one particular aspect thereof, the invention takes advantage of the observation that certain epigenetic properties of a cell's DNA correlate with the cell type and differentiation status. Particularly, the methylation patterns associated with the described genes is indicative of its identity and status. The consistency, stability and uniformity of this approach make it a useful complement to or replacement for the conventional techniques for assessing cells, which suffer from a range of disadvantages.

The inventors describe a series of genes and genetic regions whose epigenetic (e.g. methylation) patterns are statistically correlated to the type of cell. As such, these regions represent particularly sensitive and useful markers for distinguishing cell type.

More preferred is a method according to the present invention, wherein said cell is present in said biological sample in a cell population, cellular batch, a heterogeneous population of cells, a subpopulation of cells, a tissue, an organ and/or a non-human organism.

In another aspect thereof, the method according to the present invention, further comprises determining the identity, purity, cell type, cellular status, composition, relative proportion, absolute amount and/or potency of said cell based on said presence in said biological sample. The present invention thus provides methods and nucleic acids for the determination of purity, identity and potency of cells by epigenetic analysis of specific genes or genomic regions. Examples are as follows:

Identity/purity—Using the methods and nucleic acids claimed herein, it will be possible to determine the components and proportions of cell populations (i.e., cell types, cell stages, etc.) within a batch. It will also, for example, be possible to identify contaminants in the batch.

Potency—Using the methods and nucleic acids described herein, cell batches and their origins and/or growth treatment in culture can be statistically correlated to the success of the treatment. As such, the described nucleic acids and methods are to be used to assess the suitability of tissue engineering procedures and provide a way to predict the validity of cell batches. The derived knowledge should be utilised to assist patients and clinicians in determining improved treatment and tissue culturing options.

In yet another aspect of the method according to the present invention, the determining comprises calculation by an algorithm based on linear algebra. Further details regarding this are outlined below (see "Data analysis").

Preferred is a method according to the present invention, wherein one or any combination of the following cell types are analysed: keratinocytes, chondrocytes, osteoblasts, melanocytes, fibroblasts, adipocytes, or mesenchymal stem cells. The methylation profile may be, for example, employed to determine or confirm the identity of a relatively homogeneous cell sample. For example, the patterns generated by MS-SNuPE in FIG. 2 are consistent with that of essentially pure adipocytes or keratinocytes.

More preferred is a method according to the present invention, wherein said analysis of the methylation status comprises a chemical or enzymatic conversion of the DNA. Usually, chemical conversion is performed with bisulfite treatment as described herein, and enzymatic conversion is performed using methylation-sensitive restriction enzymes. In a most preferred embodiment of the method according to the present invention, the converted DNA is subsequently amplified. Such amplification preferably involves an enzymatic amplification using a polymerase enzyme, preferably a heat stable polymerase enzyme, such as a Taq polymerase. Respective methods are further described below.

In yet another aspect of the method according to the present invention, said analysis of the methylation status comprises an analysis selected from promoter methylation, CpG island methylation, and/or analysis of at least one CpG in any of the chemically converted chromosomal DNAs as shown in SEQ ID NOs 1 to 160, preferably as shown in SEQ ID NOs 76 to 160, and sequences complementary thereto.

There are a number of well-established techniques for determining the methylation status of samples that range from those for determining the overall methylation level of the genome to those that quantitatively detect the methylation level at single or closely linked CpGs. General techniques for analysis of DNA methylation are reviewed by Dahl and Guldberg, Biogerontology 4:233-50 2003. Furthermore, statistical approaches to describe, discriminate, and classify methylation patterns have been validated for various uses (reviewed by Siegmund and Laird, Methods 27:170-8, 2002).

Preferred is a method according to the present invention, wherein said analysis of the methylation status comprises at least one of the following methods: MSP, HeavyMethyl, MethyLight, Ms-SNuPE or other methods relying on a detection of amplified DNA. These methods are used in order to analyse particular regions which, in some instances, are combined in order to give information about the genome.

Most of the methods for detecting methylation differences in DNA samples rely on either of two approaches: chemical conversion or digestion with methylation-sensitive restriction enzymes. These methods are preferred, because standard molecular techniques that rely on specific base pairing (PCR, sequencing, etc.) will not specifically detect methylated cytosine nucleotides since they have the same base-pairing characteristics as unmethylated cytosines.

A first approach currently relies on a chemical called bisulfite (disulfite, hydrogen sulfite, bisulphite) that, combined with alkaline hydrolysis, converts unmethylated cytosine (C) to uracil (U), while leaving methylated C unchanged. During, for example, PCR amplification, the U's will be replaced by thymines (T's) (Frommer et al., Proc Natl Acad Sci USA 89:1827-1831, 1992). After chemical conversion, each unmethylated CpG site therefore contains an altered nucleotide sequence that can then be detected by conventional techniques, such as sequencing, single base primer extension, microarray chips, or various PCR techniques. (Note that all genomic C's that are not within a CpG motif are assumed to be converted to U's since CpG's are the overwhelming targets of methylation in vertebrates.) The main drawback of this technique is that conversion by bisulfite is not always 100% efficient, but various modifications are available to improve the efficiency (Olek et al., Nucleic Acids Res. 24:5064-6, 1996; Rein et al., Mol Cell Biol. 17:416-26, 1997; Paulin et al., Nucleic Acids Res. 26:5009-10, 1998; Warnecke et al., Methods 27:101-7, 2002).

A second approach employs restriction enzymes that cut DNA differentially depending on the methylation state of the CpG target site. Since the potential cutting targets may occur at thousands of places within the DNA, this approach is generally suited to large-scale, unbiased analysis of the entire genome. Furthermore, this method is amiable to discriminating broad changes in methylation, e.g., large segments of CpG islands that are either completely methylated or unmethylated, rather than individual CpGs. Therefore, methods relying on methylation-sensitive restriction enzymes are more useful in marker discovery—the initial determination of which regions are differentially methylated with respect to particular cell types or states—rather than as an assay method per se. Examples of such methods are RLGS (Costello et al., Nat Genet. 24:132-8, 2000), MCA (Toyota et al., Cancer Res. 59:2307-12, 1999), MS-AP-PCR (Gonzalgo et al., Cancer Res. 57:594-9, 1997) and DMH (Huang et al., Hum Mol Genet. 8:459-70, 1999).

Standard techniques to analyse DNA methylation are furthermore:

a) Bisulfite sequencing: Direct sequencing of DNA will not distinguish methylated cytosine nucleotides since they have the same base pairing characteristics as non-methylated cytosines. In bisulfite sequencing, the genomic DNA is first treated with bisulfite and then (typically) specific regions are amplified with PCR. The proportion of methylated cytosines within any particular CpG site can then be estimated by the ratio of C/T signals found at that site (Frommer et al., Proc Natl Acad Sci USA 89:1827-1831, 1992). Bisulfite sequencing is targeted to very specific segments of DNA (e.g., a particular gene) and is thus more suited for detailed analysis of particularly interesting regions since it gives information about the methylation status of every CpG in the sequenced region.

b) MSP: This method takes advantage of discriminatory priming of a PCR reaction due to the differences in the target DNA after bisulfite treatment. Briefly, two alternate primers are designed, one that anneals preferentially to the methylated version of the target CpG (which still contains a C at the target site after bisulfite treatment) and one that anneals preferentially to the unmethylated version (which contains an U at the target site after bisulfite treatment). A ratio of the originally methylated/unmethylated target sites is derived from the relative portion of amplification products (e.g., by ethidium bromide staining of an agarose gel) generated from each primer set. MSP requires only small amounts of target DNA and can detect a 0.1% methylation level (Herman et al., Proc Natl Acad Sci USA 93:9821-9826, 1996; U.S. Pat. No. 5,786, 146). However, MSP should still be considered as only semi-quantitative and most suitable for initial screening (Dahl and Guldberg, Biogerontology 4:233-50).

c) MethyLight: This technique also relies on PCR amplification of bisulfite-treated DNA with the primary improvement being the inclusion of a fluorescent hybridisation probe ("TaqMan") for detection. The probe contains both a fluorescent dye and a quencher moiety so that the fluorescence is suppressed when the probe is intact. During PCR amplification the hybridised probe is hydrolysed by the polymerase, thus releasing the fluorine. The increased fluorescence can then be detected in a real-time fluorescent detection system. Quantitation is typically achieved by determining the cycle number at which the fluorescence crosses some predetermined threshold. Specificity to methylated or unmethylated target DNA is contained in the design of the flanking primers or in the hybridisation probe itself (Eads et al., Cancer Res 59:2302-2306, 1999). MethyLight is very sensitive and capable of high throughput, but generates a low resolution (Dahl and Guldberg, Biogerontology 4:233-50).

d) HeavyMethyl: This is a variation of the MethyLight technique with a further refinement of adding methyl-specific blocking probes that interfere with hybridisation of the PCR amplification primers or the detection probe (Cottrell et al., Nucleic Acids Res 32:e10, 2004).

e) Ms-SNuPE: Ms-SNuPE is a variation of the single nucleotide primer extension method for detecting SNPs (Kuppuswamy et al., Proc Natl Acad Sci USA. 88:1143-7, 1991). The region of interest is amplified by PCR from bisulfite-treated genomic DNA such that there is no bias towards amplification of either methylated or unmethylated target DNA. A detection primer is designed to hybridise immediately adjacent to the target CpG in the resulting PCR amplicons. Reaction conditions are such that the primer can only be extended by a single nucleotide (e.g., a G or an A as complementary bases to C or T, respectively). The relative incorporation of radio- or dye-labelled nucleotides gives the ratio of methylated (G incorporated) or unmethylated (A incorporated) at that site in the original DNA. The method is both quantitative and sensitive (Gonzalgo and Jones, Nucleic Acids Res 25:2529-2531, 1997).

e) COBRA: This method makes use of specific restriction enzymes after bisulfite conversion of genomic DNA and an unbiased amplification by PCR. Since bisulfite conversion potentially destroys the native restriction sites or creates new ones, restriction enzymes can be chosen to target CpG sites that were either originally methylated or originally unmethylated, depending on the experimental design. The proportion of methylated or unmethylated nucleotides at that site can then be estimated by comparing the amount of cleaved products to the total amount of PCR product (Xiong and Laird, Nucleic Acids Res. 25:2532-2534, 1997). COBRA is a sensitive technique, but is limited to analysing CpGs that may be targeted by particular restriction enzymes (Dahl and Guldberg, Biogerontology 4:233-50).

f) MSRE-PCR: One method that does not require pretreatment of the DNA with bisulfite reagents is the analytical use of methylation-sensitive restriction enzymes targeting CpGs whose flanking DNA is then specifically amplified by PCR. Discrimination of the methylation status is generated by using isoschizomer enzymes in parallel in which one enzyme if methylation sensitive and the other is not (e.g., HpaII/MspI which both target CCGG; the site cannot be cleaved by HpaII if the internal CpG is methylated). The uncut DNA can undergo specific PCR amplification (using primers that target each side of the restriction site), while the cut DNA will not. Therefore, the relative proportion of methylation at that site can be estimated by the accumulation of PCR products from the methylation-sensitive digestion versus that from the total (i.e., undigested DNA; the methylation insensitive enzyme serves as a negative control) (Singer-Sam et al., Mol Cell Biol 10:4987-9, 1990).

g) Methylation-specific chips (DNA (micro)arrays, gene chips, genome chips): This is a means of detecting methylation differences in a large number of CpG sites (possibly associated with many different genes) simultaneously. In one method, the bisulfite or chemically converted DNA from a sample is amplified by PCR, then labelled with a fluorescent dye, such as Cy5. The methylation level originally present at each CpG site in the genomic DNA is determined by specific hybridisation to probes bound to a solid media phase (the "chip").

The bound probes can be oligonucleotides or PNA-oligomers at least 9 bp in length that are identical to or complementary to the methylation markers of interest. Probes can be designed in tandem such that one preferentially recognises an originally methylated C (amplified as an unmodified C) and the other preferentially recognises an originally unmethylated C (chemically converted and amplified as a T). That is, near the middle of the probe, one version of the pair may contain a CG and the other a TG (or a CG and CA, depending on the sense of the strand). The probes should also overlap C's at non-CpG sites in order to minimise the effects of incomplete bisulfite conversion of the sample DNA. Probes representing several hundred CpG sites may be bound to individual positions ("spots") on the solid media by a 6C-amino modification at their 5' ends.

The labelled amplicons from the sample are then hybridised to the probes under conditions that distinguish the base-pair mismatches. The unbound labelled DNA is removed and the relative fluorescent intensity is determined for each pair of spots that recognise either the originally methylated CpG or the originally unmethylated CpG for each marker site. (Golub et al., Science 286:531-557, 1999; Chen et al., Nucleic Acids Res 27:389-395, 1999).

In yet another aspect of the method according to the present invention, said method further comprises a prediction of the quality and/or suitability of said cells as therapeutics based on the analysis of the methylation status and/or epigenetic markers of said cells. In this aspect, the markers according to the present invention are used in order to monitor the suitability of the cells to be employed in a therapeutic approach (which in itself constitutes another preferred embodiment of the present invention). A factor that reflects the quality and/or suitability of said cells which can be measured by using the present markers (genes) is the viability (e.g. proliferation or general protein turnover) of the cells. Cells that appear to lack viability or show expression of markers related to transformation and/or apoptosis will usually not be used for a treatment. Markers can also be employed in accordance with statistical correlation with successful medical outcomes. In yet another similar aspect of the method according to the present invention, said method further comprises an estimation or prediction of the potency of said cells in their use as a therapeutic for an individual or between different individuals (which in itself constitutes another preferred embodiment of the present invention). Here, differences between nominally identical types of cells between individuals to be treated are examined based on the present markers. In yet another similar aspect of the method according to the present invention, said method further comprises a quality control during the development, manufacturing and approval of engineered tissues (which in itself constitutes another preferred embodiment of the present invention). In addition to characterization of identity and purity, a factor that reflects the quality of said cells which can be measured by using the present markers (genes) is the viability (e.g. proliferation or general protein turnover) of the cells. Cells that appear to lack viability or show expression of markers related to malignant transformation and/or apoptosis will usually not be used for a generation of tissues. Markers can also be employed in accordance with statistical correlation with successful medical outcomes. In yet another aspect of the method according to the present invention, said method further comprises detecting and monitoring the response to chemical and/or biological substances interacting with the cells' growth or differentiation program(s) (which in itself constitutes another preferred embodiment of the present invention). Here, a follow-up of the methylation pattern of certain cells based on the markers herein will point to changes in the cells as a response to chemical and/or biological substances, in some cases even before a phenotypic change can be observed. Cells that appear to show expression of markers related to transformation and/or apoptosis will usually not be used further or the treatment will be ceased and/or a different treatment will be initiated.

Another preferred aspect of the present invention is directed to a nucleic acid molecule, comprising a sequence at least 18 bases in length of a segment of the chemically pretreated genomic DNA derived from the genes COL3A1, CAV1, PRELP, SPP1, CHAD, ANXA6, KRTHB6, BGN, LTA, FGFR1, HIF1A, GDF5, PTHR1, BMP4, GLI3, COL2A1, IGF2, LPIN1, TDGF1, KRT8, CD4, CNTN1, COL6A3, FMOD, PKNOX2, C15orf27, ROPN1L, and ACVRL1 or according to any one of the sequences taken from the group consisting of SEQ. ID NO. 1 to 160, preferably SEQ. ID NO 76 to 160, and sequences complementary thereto.

In one preferred embodiment of the nucleic acid molecule according to the present invention, the sequence of said molecule is different from the unmodified chromosomal sequence. This embodiment reflects the fact that—although chemically treated—each unmethylated CpG site contains an altered nucleotide sequence that can then be detected by conventional techniques, such as sequencing, single base primer extension, microarray chips, or various PCR techniques, whilst all methylated C's remain unchanged (i.e. identical to the genomic sequence).

Thus, the invention provides the chemically modified genomic DNA, as well as oligonucleotides and/or PNA-oligomers for detecting cytosine methylations, as well as a method which is particularly suitable for the classification of cells by type or status. The present invention is based on the discovery of particular variations in the cytosine methylation patterns of genomic DNA that are particularly suitable for distinguishing various cell types in the mesenchymal lineage.

As mentioned above, this objective is achieved, according to the present invention, by detection of epigenetic and, in particular, methylation differences within genomic sequences according to one of SEQ ID NOs. 1 to 25, and sequences complementary thereto.

This objective is further achieved, according to the present invention, by providing a nucleic acid containing a sequence of at least 18 bases in length of the chemically pretreated genomic DNA according to one of SEQ ID NOs. 1 to 160, preferably SEQ ID NOs 76 to 160, and sequences complementary thereto. The chemically modified nucleic acids could not previously be connected with the discrimination of cell type or status.

IGF2 has been described as partaking in the phenomenon of imprinting in early development.

Preferred is an oligomer, in particular an oligonucleotide or peptide nucleic acid (PNA)-oligomer, said oligomer comprising in each case at least one base sequence having a length of at least 9 nucleotides which is complementary to, or hybridises under moderately stringent or stringent conditions to a pretreated genomic DNA as described above, and sequences complementary thereto. More preferred is an oligomer according to the present invention, wherein the nucleotide sequence of said oligomer comprises at least one CpG, TpG or CpA dinucleotide. More preferred is an oligomer according to the present invention, wherein the CpG, TpG or CpA dinucleotide is located in the middle third of the oligomer. More preferred is oligomer according to the present invention, wherein the nucleotide sequence of said oligomer terminates one base before a target CpG of either of the strands of the genomic, unconverted DNA sequence.

Another preferred aspect of the present invention is directed to a set of oligomers, comprising at least two oligomers according to the present invention and as described above.

As stated, the object of the present invention is further achieved by oligonucleotides for detecting the cytosine methylation state in chemically pretreated DNA, containing at least one base sequence having a length of at least 9 to 13 nucleotides which hybridises to a chemically pretreated genomic DNA according to SEQ ID NOs. 1 to 25, and in particular to SEQ ID NOs 76 to 160. The base sequence of the oligomers preferably contains at least one CpG, TpG or CpA dinucleotide. Particularly preferred are oligonucleotides according to the present invention in which the targeted cytosine of the CpG occurs in the middle third of the oligomer. The oligonucleotides may also exist in the form of a PNA (peptide nucleic acid) which has particularly preferred pairing properties or as dye-conjugated or other covalently modified nucleic acids.

Another preferred aspect of the present invention relates to a diagnostic kit for detecting the presence of certain cell types and statuses based on DNA methylation, comprising: a) a bisulfite reagent; and b) a nucleic acid molecule as above or an oligomer or set of oligomers according to the present invention. Thus, one preferred embodiment of the invention is the production of kits for the uses described above. The kits may contain: 1. Chemicals (bisulfite, etc.) for processing the cell samples; 2. Procedure protocols; 3. Oligonucleotide probes, blockers or extension primers according to the present invention that will detect markers relevant to a particular cell type. The oligonucleotides would be constructed to generate a signal on a commonly available detection platform, such as Real Time-PCR (RT-PCR) or Single Base Extension (SBE). Each signal indicates the level of methylation at a particular target site in the sample. As an alternative, probes according to the described nucleic acids could be produced for usage on a chip; 4. A bioinformatic tool to process the results. This, e.g., software might normalise the signals from the raw data, contain a result matrix for interpretation of the read-out, or implement various algorithms that calculate, for example, cell type proportions, or potency predictions.

Yet another preferred aspect of the present invention relates to the use of a nucleic acid molecule according to the present invention or an oligomer or set of oligomers according to the present invention or a kit according to the present invention for determining the presence of a particular cell type in a biological sample. Yet another preferred aspect of the present invention relates to the use according to the present invention, wherein said cell is present in said biological sample in a cell population, cellular batch, a heterogeneous population of cells, a subpopulation of cells, a tissue, an organ and/or a non-human organism. Yet another preferred aspect of the present invention relates to the use according to the present invention for determining the identity, cell type, cellular status, composition, relative proportion, absolute amount and/or potency of said cell based on said presence in said biological sample. Yet another preferred aspect of the present invention relates to the use according to the present invention for a quality control during the development, manufacturing and approval of engineered tissues. Yet another preferred aspect of the present invention relates to the use according to the present invention for monitoring the response to chemical and/or biological substances interacting with the cells' growth or differentiation behaviour. The genes (markers) that form the panel according to the present invention have not been used for such methods as described above, and are surprisingly well suited for precise and quick analyses.

As will be understood from reading the above, the precise analysis of cell types that is possible with the inventive markers can be applied to diagnostic and/or analytical purposes for tissues and cells in vivo.

DEFINITIONS

Gene names are according to HUGO (The Human Genome Organisation; www.gene.ucl.ac.uk/hugo). Genomic sequences and mapping are according to ENSEMBL (www.ensembl.org) release Version 35 of the human genome.

In the context of the present invention, the terms "gene(s)" and "marker(s)" are used interchangeably and relate to the nucleic acids that form the basis of the listing of genes as given in Table 1. It should be understood that the present invention is not limited to the nucleic acid sequence as depicted in the accompanying sequence listing, but also encompasses sequences of the genes as indicated that have been corrected due to sequencing errors and/or errors in mapping the genes on the chromosome.

In the context of the present invention, "expression level" or "expression analysis" comprises determination of the mRNA and/or protein expression and/or analysis of the methylation status and/or analysis of other epigenetic markers. Preferred are the analyses of methylation status and/or analysis of other epigenetic markers.

In the context of the present invention, "genetic parameters" are mutations and polymorphisms of genomic DNA and sequences further required for their regulation. To be designated as mutations are, in particular, insertions, deletions, point mutations, inversions and polymorphisms and, particularly preferred, SNPs (single nucleotide polymorphisms).

In the context of the present invention, "epigenetic parameters" are, in particular, cytosine methylations and further modifications of DNA bases of genomic DNA and sequences further required for their regulation. Further epigenetic parameters include, for example, the acetylation of histones, which cannot be directly analysed using the described method but which, in turn, correlates with the DNA methylation.

In the context of the present invention, the term "regulatory region" of a gene is taken to mean nucleotide sequences which affect the expression of a gene. Said regulatory regions may be located within, proximal or distal to said gene. Said regulatory regions include but are not limited to constitutive promoters, tissue-specific promoters, developmental-specific promoters, inducible promoters and the like. Regulatory elements may also include certain enhancer or silencer sequence elements that control transcriptional or translational efficiency of the gene.

The term "biological material" relates to any material that is derived from a source, in particular an animal and/or human source, that contains or is suspected to contain genomic DNA and/or the protein(s) of interest. One preferred example of a biological material according to the present invention is designated herein as "biological sample" or "biological specimen".

In the context of the present invention, the terms "identity", "purity" and "potency" are as employed by regulatory agencies, i.e. meaning (1) the correct labelling of a substance, (2) the kind and amount of impurities, and (3) the therapeutic or functional effectiveness of the substance, respectively.

In the context of the present invention, the term "bisulfite" (disulfite, hydrogen sulfite, bisulphite) shall mean the chemical entity that converts unmethylated cytosine (C) to uracil (U), while leaving methylated C unchanged (see, for example, Frommer et al., Proc Natl Acad Sci USA 89:1827-1831, 1992).

In the context of the present invention, the term "bisulfite sequencing" shall mean a method wherein genomic DNA is treated with bisulfite, amplified with PCR and sequenced with molecular biological techniques that account for the resulting low complexity sequence (see, for example, Frommer et al., Proc Natl Acad Sci USA 89:1827-1831, 1992).

In the context of the present invention, the term "MSP" shall mean methyl-Specific PCR, in which amplification of DNA is dependent on methylation-specific primers after bisulfite treatment (Herman et al. Proc. Natl. Acad. Sci. USA 93:9821-9826, 1996; U.S. Pat. No. 5,786,146).

In the context of the present invention, the term "MethyLight" shall mean the technique in which PCR amplification of bisulfite-treated DNA is detected by fluorescent hybridisation probe during Real-Time PCR (Eads et al., Cancer Res. 59:2302-2306, 1999).

In the context of the present invention, the term "HeavyMethyl"—shall mean the variation of the MethyLight technique also employing adding methyl-specific blocking probes (Cottrell et al., Nucleic Acids Res 32:e10, 2004).

In the context of the present invention, the term "MS-SnuPE" shall mean Methylation-Sensitive Single Nucleotide Primer Extension follows PCR amplification of bisulfite-treated genomic DNA and detects the ratio of methylated to unmethylated C's by differential incorporation of a nucleotide on a primer that hybridises immediately adjacent to the target CpG (Gonzalgo and Jones, Nucleic Acids Res. 25:2529-2531, 1997).

In the context of the present invention, the term "COBRA" shall mean Combined Bisulfite Restriction Analysis which employs restriction enzymes targeting potential methylation sites that might be created or destroyed by bisulfite conversion of DNA. Uncleaved template is quantitated by subsequent local amplification of the flanking sequences (Xiong and Laird, Nucleic Acids Res. 25:2532-2534, 1997).

In the context of the present invention, the term "MSRE-PCR" shall mean Methylation-sensitive Restriction Endonuclease which uses methylation-sensitive restriction enzymes targeting CpGs on unconverted genomic DNA. Uncleaved template is quantitated by subsequent local amplification of the flanking sequences (Singer-Sam et al., Mol Cell Biol. 10:4987-9, 1990).

In the context of the present invention, the terms "Chips", "DNA microarrays", "gene chips", "genome chips" shall mean a device that helps to detect the methylation status of, for example, bisulfite-converted and PCR amplified DNA fragments by differential hybridisation to probes bound to a solid media phase. Paired probes contain alternative nucleotides that are complementary to CpG sites depending on whether they were converted or not (i.e., unmethylated or methylated) by chemical treatment. The hybridised DNA fragments are typically detected via a fluorescent dye covalently attached to the fragment (Golub et al., Science 286:531-557, 1999; Chen et al., Nucleic Acids Res 27:389-395, 1999; an overview of chip manufacture is given in Nature Genetics Supplement, Volume 21, January 1999).

In the context of the present invention, the term "cell type" shall mean the commonly accepted label for a cell according to its lineage and differentiation status, generally according to common phenotyping methods (histology, etc.). However, it shall be understood that the precision of DNA methylation analysis may lead to new subtypes or a re-characterization of accepted cell type labels which, in turn, will lead to new cell types.

In the context of the present invention, the term "cell status/stage" shall mean potentially variable characteristics of a cell including general health, differentiation state, cell age, alterations during generations or passages, competence for propagation, differentiation, apoptosis, therapeutic potency, etc.

"Stringent hybridisation conditions", as defined herein, involve hybridising at 68° C. in 5×SSC/5×Denhardt's solution/1.0% SDS, and washing in 0.2×SSC/0.1% SDS at room temperature, or involve the art-recognised equivalent thereof (e.g., conditions in which a hybridisation is carried out at 60° C. in 2.5×SSC buffer, followed by several washing steps at 37° C. in a low buffer concentration, and remains stable).

Moderately stringent conditions, as defined herein, involve including washing in 3×SSC at 42° C., or the art-recognised equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In the context of the present invention, the term "genomic DNA" shall mean native DNA before any chemical treatment.

In the context of the present invention, the term "CpG" shall indicate the typical target sequence for methylation in vertebrate genomes, with the cytosine undergoing methylation (or not).

In the context of the present invention, the term "converted" or "chemically (pre)treated DNA" shall mean DNA subjected to a chemical treatment (e.g., bisulfite) that alters the base-pairing characteristics depending on methylation status of the nucleotides.

In the context of the present invention, the terms "oligos", "oligonucleotides", "oligomers" are used interchangeably and indicate oligonucleotides with or without modification by dyes, minor groove binders (Zeschnigk et al., Nucleic Acids Res 32:e125, 2004) or other moieties, or as a peptide nucleic acid (PNA; reviewed by Pellestor and Paulasova, Eur J Hum Genet 12:694-700, 2004).

In the context of the present invention, the term "methylation level" shall mean the quantitative level of methylation at a single CpG across every DNA molecule in the sample (terminology from Siegmund and Laird, Methods 27:170-8, 2002).

In the context of the present invention, the term "methylation profile" shall mean the methylation levels at multiple sites (terminology from Siegmund and Laird, Methods 27:170-8, 2002). Similarly, a "methylation pattern" shall mean the general pattern of methylation of a sample or a subset that is characteristic for a particular cell type or status.

In the context of the present invention, the term "amplicon" shall mean the DNA fragment resulting after PCR amplification, also known as an "amplificate".

In the context of the present invention, the term "probes or blockers" shall mean oligonucleotides that specifically hybridise to DNA as a method of detection, or to interfere with the hybridisation of other oligonucleotides (Yu et al., BioTechniques 23:714-720, 1997), respectively.

As described, the present invention in general relates to the identification and characterisation of cell samples based on the analysis of methylation patterns within the genomic regions described herein. It has surprisingly been determined that these methylation patterns have a distinctiveness and consistency that gives them a utility as novel discriminatory markers for research and therapeutic purposes.

One preferred embodiment is the methylation analysis of any of the genes of contained within the listing of genes as given in Table 1, and/or particular regions thereof with or without chemical modification of the DNA using, for example, methylation-sensitive restriction enzymes, bisulfite or chemical pretreatment, PCR amplification primers, specific hybridisation probes, mass spectrometry, etc.

Another preferred embodiment provides the use of oligonucleotides or modified oligonucleotides according to the present invention that can be used for the detection of the methylation state within the region of SEQ ID NOs 1 to NO 153 or in the listing of genes as given in Table 1, for example, by way of using the oligonucleotides or modified oligonucleotides as amplification primers, extension primers, detection probes, hybridisation blockers, for hybridisation on a solid media (e.g., as in DNA chips), etc.

In particular, these primers would overlap, or be adjacent to a CpG, TpG, CpA that corresponds to a CpG site in the original genomic DNA as described in SEQ ID NOs 1 to 25.

The preferred method to distinguish methylation status of the DNAs as described in SEQ ID NOs 1 to 25 generally follows these steps:

a) Biological samples are obtained from cell cultures, biopsies, etc., using standard techniques known to the art.

b) DNA is extracted from the samples using, e.g., methods standard to the art.

[At this point, it is possible to utilise methods that do not require bisulfite or chemical pretreatment, such as MSRE-PCR, as described above.]

c) The DNA is chemically or biologically converted such that there is an altered pairing behaviour of methylated nucleotides versus methylated nucleotides, as, for example, with bisulfite treatment to convert unmethylated cytosines to uracil.

d) Specific DNA regions as described in SEQ ID NOs 76 to 160 or belonging to the genes as described above are amplified by PCR. In one preferred embodiment, the PCR amplification may be biased by methylation-specific primers, i.e., primers that hybridise to potentially methylated sites that may or may not have been altered during the chemical pretreatment (i.e., they overlap a CpG site, as described for MSP, above). Afterwards, the resulting fragments are subject to detection or quantitation methods such as gel electrophoresis analysis, hybridisation analysis, incorporation of detectable tags within the PCR products, fluorescent dye/quencher probes, etc.

In other methods, the DNA regions are amplified in an unbiased manner with regard to whether the DNA was originally methylated or unmethylated. Generally, these primers overlap some non-CpG cytosines coded in the genomic sequence to favour template DNA that was completely converted by the bisulfite reaction; i.e., the primer is designed to hybridise to T's that were C's in the native genomic DNA.

For methods in which the chemically-treated DNA was amplified in an unbiased manner, there are an number of preferred methods for detecting the original methylation state of the genomic DNA.

One preferred detection method is direct (bisulfite) sequencing. This generally requires a further sequencing reaction such as cycle sequencing and analysis on an instrument for determining the nucleotide sequence of the DNA fragment (e.g., an ABI 3100 machine). The methylation level at any particular CpG site is obtained from the intensity of the C and/or T signals (for the sense strand, however these methods could also target G to A changes depending on the strand tested). Normalization of the signals and accounting for incomplete conversion of the bisulfite reaction may require elaborate software. This method gives the methylation status of multiple CpGs within the amplified sequence and has a resolution of at least 20% (Lewin et al., Bioinformatics 20:3005-12, 2004).

Another preferred embodiment is a single nucleotide primer extension reaction (a version of MS-SNuPE as described above) which detects the ratio of methylated to unmethylated cytosines at a single CpG site within the original DNA sample pool. In this case, a primer is designed to hybridise immediately adjacent to the CpG of interest such that an extension of the primer in the 5' to 3' direction incorporates the complement of the C position as the next nucleotide. The reaction conditions are such that only that nucleotide is incorporated (e.g., by using dideoxy-nucleotides or using separate reactions containing only 1 nucleotide). Thus, the ratio of methylation at that CpG position is given by the relative incorporation of C/T for the sense strand and G/A for the anti-sense strand. The relative ratios can be detected within the extended-primer products, for example, by radiometric assays of radio-labelled nucleotides, fluorescent detection of conjugated dyes, or High Performance Liquid Chromatography (HPLC) (El-Maarri, Methods Mol Biol. 287:195-205, 2004; El-Maarri et al., Nucleic Acids Res. 30(6):e25, 2002).

Detection can also be accomplished by a number of PCR methods, including Real-Time PCR (Heid et al., Genome Res. 6:986-994, 1996) in which the accumulation of a particular target product is measured by a fluorescence detection mechanism, such as in the MethyLight and HeavyMethyl methods described above. In some instances, the target sequence for primers, hybridisation probes or blocking probes may overlap several nearby CpG sites, thereby generating specificity for multiple methylated or unmethylated sites.

Many of these methods allow for multiplexing—the ability to simultaneously detect multiple probes targeting several different CpG sites. For single nucleotide primer extension, this requires that the primers have distinctive masses (different lengths or attached chemical moieties) and RT-PCR requires probes with dye moieties that have different spectral characteristics.

Other potential detection methods that have been employed for discriminating the methylation-specific fragments include mass spectrometry (Karas and Hillenkamp, Anal Chem 60:299-301, 1988; Schatz et al., Nucleic Acids Res 32:e167, 2004; Tost J et al., Nucleic Acids Res 31:e50, 2003), HPLC (El-Maarri, Methods Mol Biol 287:195-205, 2004; Baumer, Methods 27:139-43, 2002), hybridisation/melting temperature analysis (Worm et al., Clinical Chemistry 47:1183-1189, 2001; Olek et al., WO 99/28498), gel electrophoresis analysis, and DNA microarray analysis.

Once the methylation profile at one or more marker sites is determined for a sample, a number of data analysis methods are available, depending on the purpose of the assay. Examples for such a data analysis are as follows:

1. The methylation profile may be employed to determine or confirm the identity of a relatively homogeneous cell sample. For example, the patterns generated by MS-SNuPE in FIG. 2 are consistent with that of essentially pure adipocytes or keratinocytes. Methylation profiles that deviate from that predicted by the combination of markers in our marker set are unlikely to be homogeneous samples of the expected cell type. This type of analysis would be useful in, for example, quality control of in vitro manipulated cell samples that might be employed in surgical re-implantation of chondrocytes, or batches of cells used for drug screens.

2. The relative proportion of cell types in a sample can be estimated by comparing the methylation profile of the entire sample to that expected for each of the relevant cell types. In a preferred example, the calculation requires solving multiple simultaneous equations with linear algebra in the form:

$$M_1 = ax_{1a} + bx_{1b} + \ldots nx_1n$$

$$M_2 = ax_{2a} + bx_{2b} + \ldots nx_2n$$

$$\ldots$$

$$M_i = ax_{ia} + bx_{ib} + \ldots nx_{in}$$

where $M_I$ is the observed methylation level at marker I for the sample (up to i markers), $x_{IN}$ is the expected methylation level at marker I in cell type N, and a, b, . . . n are the calculated (unknown) fractions of n cell types within the sample. The calculation requires n−1 distinctive markers (assuming each marker acts at only one branch of distinction) to solve the system of equations that also includes the formula:

$a+b+\ldots n=1$ (i.e., the total of each of the cell types constitute 100% of the sample)

For example, three cell types, A, B and C, have the methylation phenotypes of (0%, 0%), (0%, 100%) and (100%, 100%) for Markers 1 and 2, respectively. For an unknown mixture containing A, B and C, the measured methylation levels for Marker 1 is 0.5 and for Marker 2 is 0.75. Therefore, the equations to be solved are:

$0.5 = a(0) + b(0) + c(1.0)$ $0.75 = a(0) + b(1.0) + c(1.0)$ $a + b + c = 1$

Solving these equations shows that the proportion of cell type A (represented by "a") is therefore 25% of the mixture, B is 25% and C is 50%.

In cases where insufficient markers or unknown/uncharacterised cell types are involved, the methylation profile sets boundary conditions, e.g., the maximum fraction of cell type A is determined by the observed methylation level and the expected methylation level for the limiting marker(s) in cell type A.

3. Detection of contaminating cell types is generally determined by a sensitive PCR detection technique (such as MethyLight or HeavyMethyl) by targeting a particular CpG or closely linked CpGs with a distinctive methylation pattern. The fraction of the original DNA molecules in the sample (i.e., representing a particular cell type) is calculated from the cycle number at which the PCR signal surpasses a predetermined threshold. These techniques approach a sensitivity in the range of 1 in 10,000 (Cottrell et al., Nucleic Acids Res 32:e10, 2004; Eads et al., Cancer Res. 59:2302-2306, 1999). This application may be useful in detecting either desirable (e.g., rare stem cells) or undesirable (e.g., cancerous or wrongly differentiated) cell types.

4. The potency of a batch of cells can be judged by statistically correlating methylation patterns with, for example, particular therapeutic outcomes. Methods to produce models for class prediction (also called supervised learning) have been previously applied to both gene expression and to methylation analysis (Adorjan P et al., Nucleic Acids Res 2002 30:e21, 2002; Golub et al., Science 286:531-557, 1999; reviewed by Siegmund and Laird, Methods 27:170-8, 2002). A prime advantage of this approach is that it relies on statistical analysis, but is not dependent on a priori knowledge of biochemical pathways, therapeutic mechanisms, etc.

The goal of this approach is to build a statistical model that targets methylation profiles that are predictive of a particular class, then to assign unknown samples into one of the classes based solely on its methylation pattern. As an example using the case of chondrocyte therapy, the methylation patterns from batches that were used in chondrocyte transplantation would be segregated into those that resulted in a positive medical outcome and those which did not. A predictive algorithm (a "classifier") is produced that essentially encapsulates a model of "good" versus "bad" chondrocyte batches. Subsequent batches of chondrocytes can be classified with this predictive model in order to filter out those batches which are not likely to be successful.

5. The analysis of methylation profiles may also be useful for tracking differentiation during in vitro manipulations of cells. For example, a researcher may desire to maintain a particular cell type during growth and expansion of a cell culture. The current usage of chondrocytes illustrates such a case: biopsy material is taken from damaged cartilage, the chondrocytes are released from the extracellular matrix by enzymatic digestion, and grown as a 3-D pellet culture to produce more cells for surgical re-implantation (Brittberg et al., J Bone Joint Surg Am 85-A Suppl 3:109-15, 2003; Brittberg et al., N Engl J Med 331:889-95, 1994). Since native chondrocytes do not normally multiply, this procedure entails some cellular alterations. Testing the methylation patterns of in vitro grown chondrocytes is one mechanism to ensure that the endpoint cells retain their original chondrocyte-like character. This is particularly useful because conventional markers (e.g., Col2A1 antibodies) used to judge the quality of chondrocytes are of dubious merit (Kolettas et al., J Cell Sci 108:1991-9, 1995; Dell'Accio et al., Arthritis Rheum 44:1608-19, 2001).

Conversely, a researcher may wish to convert one cell type (e.g., a precursor cell) to another cell type by in vitro manipulation (e.g., by using growth or differentiation factors). Such a process can be quality controlled or optimised using methylation markers to assay or track the changes. For example, mesenchymal stem cells (MSCs) may act as a precursor which can be differentiated to chondrocyte cells under the proper growth conditions (Mackay et al., Tissue Eng 4:415-28, 1998). Methylation markers that distinguish MSCs from chondrocytes are useful to monitor the progress of the conversion, ensure proper differentiation, and improve the growth/differentiation process. Thus, this invention provides novel epigenetic markers and oligonucleotides, as well as methods for testing the identity and quality of cell samples, and to optimise laboratory procedures for engineering or manipulating cells and tissues. The markers and methods have advantages over conventional molecular and morphological techniques in that they provide stable, consistent, sensitive, quantifiable and potentially universal mechanisms for discriminating a wide range of cell types.

The inventors have identified specific genomic regions which had covalent modifications specifically depending on the type or state of the cells. The invention therefore provides a set of molecular markers whose expression, and, in particular, methylation pattern is sensitive to cell type and/or status. The invention also discloses a method to identify cell and to calculate the proportion of cell types in a heterogeneous mixture.

The described invention provides a method and nucleic acids for the discrimination of cell types and statuses based on epigenetic differences. The invention discloses a means of: quantitating the portions of various cell types in a mixture; detecting minute impurities of one or more cell types within a batch; estimating the potency of a batch of cells by a statistical correlation between epigenetic markers and therapeutic outcomes or known biological parameters; and monitoring changes in cell type/status during various protocols.

The invention represents an advancement over state of the art methods (histological, immunological or mRNA detection) in that it is uniform, consistent, robust, sensitive, potentially universal and capable of producing complex information to any arbitrarily high level of resolution.

The inadequacy of current cell identification techniques means that it is difficult both to efficiently engineer the cells and, ultimately, to guarantee that engineered cells are in concordance to their original, healthy counterparts. Particularly for cells used as therapeutics, it is mandatory that their identity, purity and potency be determined prior to re-introduction into the body. Furthermore, successful cell engineering requires the ability assess growth and differentiation inducing/inhibiting factors by their effect on cell differentiation.

Methylation analysis has qualities that potentially make it superior to other methodologies for tissue recognition. Biochemical and immunological methods require long developmental times and are relevant only for particular subsets of tissues, whereas methylation testing is uniform (only the marker set varies) and universal (applicable to all tissue types). Only RNA-based arrays have strengths similar to methylation analysis in genome-wide detection of altered properties. However, RNA-based methods are problematic for a number of reasons: RNA is unstable, making it inconsistent and difficult to work with; RNA expression fluctuates in response to short-term environmental stimuli; and RNA expression analysis relies entirely on quantitative differences, therefore requiring elaborate statistical tools to assign significance to changes in mRNA expression (Miller et al., Cancer Cell 2:353-61, 2002; Nadon and Shoemaker, Trends Genet 18:265-71, 2002; Murphy D, Adv Physiol Educ, 26:256-70, 2002). Finally, although RNA arrays are powerful discovery tools, they are cumbersome for large scale clinical assays, requiring extensive panels of expression markers for class prediction (van de Vijver M J et al., N Engl J Med 347:1999-2009, 2002). Although mRNA- and methylation-based class prediction can perform comparably in cancer diagnosis, assays based on methylation are likely to be more reproducible in large scale analyses (Adorjan P et al., Nucleic Acids Res 2002 30:e21, 2002; Golub et al., Science 286:531-557, 1999).

In addition to uniformity and universality, methylation analysis is: robust, since it is based on DNA rather than RNA; sensitive, since DNA can be amplified, and informationally complex since there are millions of potential methylation sites in the human genome that can be assayed. Furthermore, since methylation levels are not an open ended signal (as in protein or mRNA expression), but rather vary from 0 to 1.0, the relative proportion of the overall signal contributed by different cell types can be calculated. Finally, the most significant advantage of methylation assays is a purely biological one. Protein- and RNA-based methodologies may reflect only the immediate, short term state of the cell; these signals are unstable and highly variable depending on the current conditions. Methylation appears to act in some cases as a long term cellular landmark, generating a stable signal that parallels the commitment to an particular cell type.

BRIEF DESCRIPTION OF THE DRAWINGS

The invention will now be further described based on the following examples and with reference to the accompanying figures and the sequence protocol.

Figure 1:
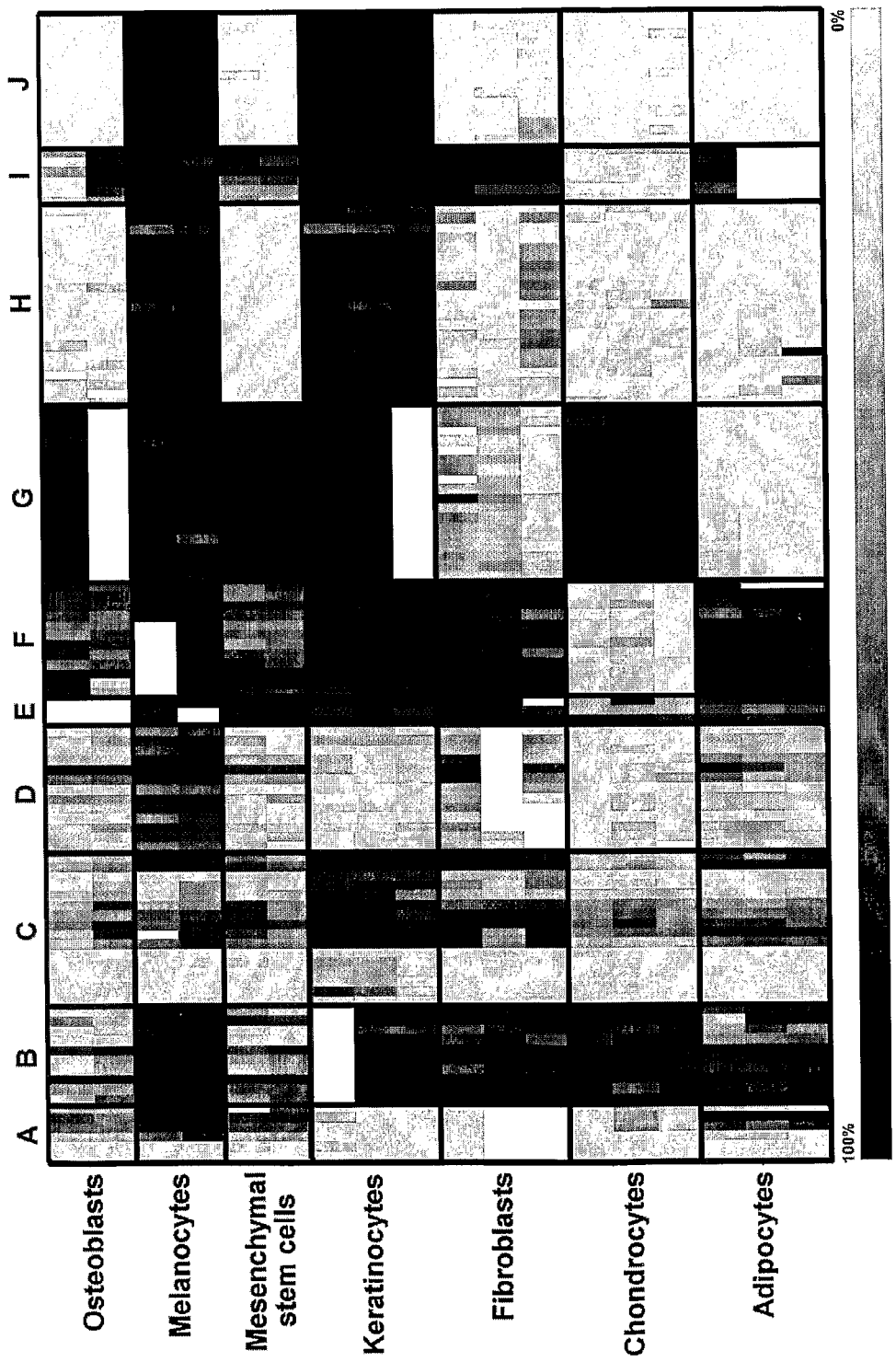
FIG. 1. Shows methylation patterns from 10 genes (A to J) in seven different cell types. Gene A=CAV1; Gene B=SPP1; Gene C=FGFR1; Gene D=ANX6; Gene E=GLI 3; Gene F=FMOD; Gene G Col3A1; Gene H=GDF5; Gene I=HIF 1A, and Gene J=

SEQ ID NO 1 to 25 depict genomic (unconverted) DNA sequences (entire genes+promoter) corresponding to the list of genes as mentioned in Table 1, below.

SEQ ID NO 26 to 75 depict bisulfite converted (chemically pretreated) DNA sequences corresponding to either fully methylated or fully unmethylated genomic DNA in the regions of variable methylation, and also sequences complementary thereto.

SEQ ID NO 76 to 101 depict the genomic (unconverted) sequences of 26 specific regions that were tested.

SEQ ID NO 102 to 153 depict the bisulfite converted (chemically pretreated) DNA sequences of 26 specific regions that were tested.

SEQ ID NO 154 to 160 depict the genomic (unconverted) sequences of additional 7 specific regions that were tested

TABLE 1

Gene (marker) list according to the present invention

| Gene name | SEQ ID NO | Accession number (GenBank) | notes: e.g., methylation patterns particular to certain subsets of cells relative to the other cell types |
|---|---|---|---|
| COL3A1 | 1, 26, 27, 76, 102, 103 | X15332 | e.g. unmethylated in adipocytes |
| CAV1 | 2, 28, 29, 77, 104, 105 | NM_001753 | e.g. heavily methylated in melanocytes; e.g. unmethylated in keratinocytes |
| PRELP | 3, 30, 31, 78, 106, 107 | BC032498 | e.g. sensitive to growth/differentiation factors; e.g. least methylated in chondrocytes and MSCs |
| SPP1 | 4, 32, 33, 79, 108, 109 | NM_000582 | e.g. distinctive for osteoblasts and MSCs |
| CHAD | 5, 34, 35, 80, 110, 111 | U96767 | e.g. heavily methylated in melanocytes; e.g. sensitive to growth conditions and growth/differentiation factors |
| ANXA6 | 6, 36, 37, 81, 112, 113 | J03578 | e.g. heavily methylated in melanocytes; e.g. sensitive to growth/differentiation factors |
| KRTHB6 | 7, 38, 39, 82, 114, 115 | X99142 | e.g. heavily methylated in keratinocytes; least methylated in melanocytes |
| BGN | 8, 40, 41, 83, 116, 117 | AK092954 | e.g. heavily methylated in fibroblasts, distinctive versus melanocytes; e.g. sensitive to growth conditions and growth/differentiation factors |

TABLE 1-continued

Gene (marker) list according to the present invention

| Gene name | SEQ ID NO | Accession number (GenBank) | notes: e.g., methylation patterns particular to certain subsets of cells relative to the other cell types |
|---|---|---|---|
| LTA | 9, 42, 43, 84, 118, 119 | X01393 | e.g. heavily methylated in chondrocytes |
| FGFR1 | 10, 44, 45, 85, 120, 121, 155 | M34185 | e.g. heavily methylated in ceratinocytes; e.g. unmethylated in chondrocytes; e.g. sensitive to growth conditions; distinguishes between chondrocytes and synovial fibroblasts |
| HIF1A | 11, 46, 47, 86, 122, 123, 156 | U22431 | e.g. unmethylated in chondrocytes; e.g. sensitive to growth conditions and growth/differentiation factors; distinguishes between chondrocytes and synovial fibroblasts |
| GDF5 | 12, 48, 49, 87, 124, 125 | X80915 | e.g. methylated in keratinocytes and melanocytes; low methylation in all others |
| PTHR1 | 13, 50, 51, 88, 126, 127 | NM_000316 | e.g. heavily methylated in keratinocytes; unmethylated in all others except melanocytes |
| BMP4 | 14, 52, 53, 89, 128, 129 | AF035427 | e.g. least methylated in chondrocytes and MSCs |
| GLI3 | 15, 54, 55, 90, 130, 131 | NM_000168 | e.g. least methylated in chondrocytes and adipocytes; e.g. sensitive to growth conditions |
| COL2A1 | 16, 56, 57, 91, 132, 133 | X16468 | e.g. heavily methylated in melanocytes |
| IGF2 | 17, 58, 59, 92, 134, 135 | NM_000612 | e.g. least methylated in keratinocytes |
| LPIN1 | 18, 60, 61, 93, 136, 137 | D80010 | e.g. most methylated in keratinocytes and fibroblasts |
| TDGF1 | 19, 62, 63, 94, 138, 139 | M96955 | e.g. heavily methylated in keratinocytes and melanocytes |
| KRT8 | 20, 64, 65, 95, 140, 141 | BC000654 | e.g. unmethylated in keratinocytes |
| CD4 | 21, 66, 67, 96, 142, 143 | M35160 | e.g. unmethylated in MSCs, distinguishing versus osteoblasts; e.g. sensitive to growth conditions |
| CNTN1 | 22, 68, 69, 97, 144, 145 | Z21488 | e.g. unmethylated in chondrocytes |
| COL6A3 | 23, 70, 71, 98, 146, 147 | X52022 | e.g. methylated in keratinocytes and melanocytes; unmethylated in all others |
| FMOD | 24, 72, 73, 99, 148, 149, 154 | U05291 | e.g. unmethylated in chondrocytes; distinguishes between chondrocytes and synovial fibroblasts |
| ACVRL1* | 25, 74, 75, 100, 101, 150, 151, 152, 153 | L17075 | e.g. heavily methylated in melanocytes |
| KRT 8 | 157 | NT_029419 | distinguishes between chondrocytes and synovial fibroblasts |
| PKNOX2 | 158 | NT_033899 | distinguishes between chondrocytes and synovial fibroblasts |
| C15orf27 | 159 | NT_010194 | distinguishes between chondrocytes and synovial fibroblasts |
| ROPN1L | 160 | NT_006576 | distinguishes between chondrocytes and synovial fibroblasts |

*Note that two widely separated areas of variable methylation were identified for this gene.

Table 3 Methylation levels and variability of selected CpGs. The average % methylation and standard deviation for three samples within each cell type (except MSCs) is shown for selected CpGs. CpGs shown in bold are considered as primary discriminators between at least two cell types and those shown in red were further characterized with MS-SNuPE. Cell type abbreviations: Keratinocytes (K), Melanocytes (M), Adipocytes (A), Chondrocytes (C), Fibroblasts (F) and mesenchymal mtem cells (MSCs)

TABLE 3

Methylation levels and variability of selected CpGs.

| | A | F | K | M | C | MSC | Distinguishes: |
|---|---|---|---|---|---|---|---|
| COL6A3: 272 | 0 (0) | 18 (20) | 95 (1) | 96 (4)* | 4 (4) | 0 | A, C, (F) from K, M |
| CAV1: 218 | 96 (8) | 21 (20) | 9 (15) | 100 (0) | 67 (41) | 79 | K from M |
| COL3A1: 328 | 0 (0) | 25 (35) | 100 (0) | 100 (0) | 100 (0) | 100 | A, (F) from K, M, C |
| BGN: 225 | 0 (0) | 100 (0) | 97 (5) | 0 (0) | 0 (0) | NA | A, M, C from F, K |
| HIF1A: 319 | 100 (0) | 100 (0) | 100 (0) | 100 (0) | 12 (19) | 71 | A, F, K, M from C |
| GDF5: 285 | 0 (0) | 14 (18) | 98 (0) | 100 (0) | 0 (0) | 0 | A, C, (F) from K, M |
| ANXA6: 264 | 46 (1) | 42 (40) | 7 (8) | 100 (0) | 0 (0) | 42 | M from C |
| SPP1: 157 | 91 (2) | 100 (0) | 100 (0) | 99 (1) | 97 (4) | 67 | (A, F, K, M, C from MSC) |

The average % methylation and standard deviation for three samples within each cell type (except MSCs) is shown for selected CpGs.
CpGs shown in bold are considered as primary discriminators between at least two cell types and those shown in red were further characterized with MSSNuPE.
Cell type abbreviations:
Keratinocytes (K),
Melanocytes (M),
Adipocytes (A),
Chondrocytes (C),
Fibroblasts (F) and
mesenchymal mtem cells (MSCs)

EXAMPLES

Example 1

According to the present invention, the methylation status of particular regions of certain genes (as disclosed in SEQ ID NO. 1 to 25 and in Table 1) were found to have differential expression levels and methylation patterns that were consistent within each cell type.

The analysis procedure was as follows. Approximately 150 genes were chosen for analysis based on suspected relevance to particular cell types or cell states according to scientific literature. In general, the candidates were selected from conventional markers for specific cell types, those showing strong or consistently differential expression patterns, or genes associated with diseases in particular tissues (Winter et al., Arthritis Rheum 48:418-29, 2003; Dell'Accio et al., Arthritis Rheum 44:1608-19, 2001; Benz et al., Biochem Biophys Res Commun 293:284-92, 2002; Tremain et al., Stem Cells 19:408-18, 2001; Wieczorek et al., Cell Tissue Res 311:227-37, 2003; Imabayashi et al., Exp Cell Res 288: 35-50, 2003; Peng et al., J Cell Biochem 90:1149-65, 2003; MacDougald and Lane, Annu Rev Biochem 64:345-73, 1995; Shum and Nuckolls, Arthritis Res 4:94-106, 2002; R&D and Chemicon online catalogues), or from keywords in the Gene Ontology or SwissProt databases. Alternatively, candidate genes can be identified by discovery methods, such as MCA.

The candidates targeted predominantly chondrocytes with only a few (<10) specific to adipocytes, osteoblasts or mesenchymal stem cells. In only very few cases has the expression pattern or relevance of the gene in other cell types been previously demonstrated. Furthermore, there was little reason to suspect that differential methylation patterns would be found between cell types for which the candidates were not targeted, like keratinocytes or melanocytes.

Generally, two PCR amplicons (200-500 base pairs long) were designed for each gene, but mainly due to the low complexity of bisulfite-treated DNA and the requirement to avoid CpG sites within the primer (which may or may not be methylated), primers for only approximately 250 amplicons were designed and created.

In most cases, DNA from at least three independent samples (representing standard examples of the cell types as might be obtained routinely by purchase, biopsy, etc.) for each known cell type were isolated using the Qiagen DNeasy Tissue Kit (catalog number 69504), according to the protocol "Purification of total DNA from cultivated animal cells". This DNA was treated with bisulfite and amplified using primers as designed above.

The amplicons from each gene from each cell type were bisulfite sequenced (Frommer et al., Proc Natl Acad Sci USA 89:1827-1831, 1992). The raw sequencing data was analysed with a program that normalises sequencing traces to account for the abnormal lack of C signal (due to bisulfite conversion of all unmethylated C's) and for the efficiency of the bisulfite treatment (Lewin et al., Bioinformatics 20:3005-12, 2004).

For each of the described gene regions, at least 1 CpG site showed significant distinctions between some pair of cell types (examples are shown in FIG. 1). FIG. 1 thus summarises the methylation data for 10 exemplary genomic regions (each associated with a different gene) in a comparison between 7 cell types. Each vertical block (labelled A-J) is a particular genomic region, with each individual column representing a single CpG site. Each horizontal block (e.g., "osteoblasts") represents a particular cell type, with each individual row representing an independent sample of that cell type. Each cell of the matrix therefore represents the average methylation level of that sample at one particular CpG site, according to the colour bar at the bottom (yellow (light grey)=low methylation; blue (dark grey)=heavy methylation; variable green (intermediate shadings of grey)=intermediate levels of methylation). Note that, for the present purposes, a single distinctive CpG within each gene is sufficient to serve as a marker. The statistical significance was generally determined by the Fisher criteria, which compares the variation between classes (i.e., different cell types) versus the variation within a class (i.e., one cell type).

While all of these markers carry useful information in various contexts, there are several subclasses with potentially variable utility. For example, COL6A3, FMOD, COL3A1, GDF5, and HIF1A typically show large blocks of consecutive CpGs which are either strongly methylated or strongly unmethylated in many cell types. Because of their 'all-or-none' character, these markers are likely to be very consistent and easy to interpret for many cell types. In other cases, the discriminatory methylation may be restricted to one or a few CpGs within the gene, but these individual CpGs can still be reliably assayed, as with single base extension. In addition to markers that show absolute patterns (i.e., nearly 0% or 100% methylation), markers/CpGs that are consistently, e.g., 30% methylated in one cell type and 70% methylated in another cell type are also very useful.

Some marker regions may be most applicable to or most distinctive for specific subsets of cell types. For example, CHAD, COL2A1, CAV1, ACVRL1 and ANXA6 are most heavily methylated in melanocytes, while PTHR1, KRT9 and FGFR1 are most heavily methylated in keratinocytes (among the cell types tested here). Conversely, genes FMOD, FGFR1, HIF1A and CNTN1 are least methylated in chondrocytes, COL3A1 is least methylated in adipocytes, KRT8 and CAV1 are least methylated in keratinocytes, KRT9 the least in melanocytes, and CD4 the least in Mesenchymal Stem Cells (MSCs). Keratinocytes and melanocytes are methylated in PTHR1 and COL6A3, while all the other cell types were not. Gene SPP1 is distinctive for osteoblasts among the differentiated cell types tested. Heavy methylation in GDF5 separates keratinocytes and melanocytes from all other cell types except osteoblasts (which is weakly methylated). CAV1 appears most useful in separating melanocytes from keratinocytes, while BGN appears most useful in separating melanocytes from fibroblasts, and FGFR1 for separating chondrocytes from keratinocytes.

One possible use of the markers would be to distinguish one particular cell type from another in a mixture, for example as the result of a growth or differentiation process. Table 2 shows examples of markers that would be most discriminatory between any specific pair of cell types, and which marker(s) may be most distinctive for one cell type versus all or most of the others. In some cases, 2 or 3 markers might be sufficient to identify and quantitate the cell types.

TABLE 2

Most distinctive markers for any pair of cell types and the most distinctive individual marker(s) for any cell type versus all or most of the other cell types.

|  | osteoblasts | MSCs | chondrocytes | adipocytes | fibroblasts | keratinocytes | melanocytes | Most distinctive individual marker(s) |
|---|---|---|---|---|---|---|---|---|
| osteoblasts | — | ANXA6 | SPP1, HIF1A, FMOD, ANXA6, KRT8 | SPP1, COL3A1 | SPP1, BGN, CHAD | COL6A3, PTHR1, GDF5 | CHAD, COL6A3, GDF5, COL2A1 | SPP1 |
| MSCs |  | — | SPP1, FMOD, HIF1A, KRT8 | COL3A1, CNTN1, SPP1 | HIF1A, SPP1, FMOD, CHAD, COL3A1 | PTHR1, COL6A3, GDF5, FGFR1 | CHAD, COL6A3, GDF5 | SPP1 |
| chondrocytes |  |  | — | FMOD, CNTN1, HIF1A, COL3A1 | BGN, FMOD, CNTN1, HIF1A | PTHR1, COL6A3, GDF5, FGFR1, FMOD, CNTN1, HIF1A | CHAD, COL6A3, GDF5, ANXA6, FMOD, CNTN1, HIF1A | FMOD, HIF1A |
| adipocytes |  |  |  | — | BGN, CAV1 | PTHR1, COL6A3, GDF5, COL3A1, FGFR1 | COL6A3, GDF5, COL3A1 | COL3A1 |
| fibroblasts |  |  |  |  | — | PTHR1, COL6A3, GDF5 | COL2A1, COL6A3, GDF5, BGN | BGN |
| keratinocytes |  |  |  |  |  | — | CAV1, ANXA6, KRT8, COL2A1 | CAV1, KRT8 |
| melanocytes |  |  |  |  |  |  | — | COL2A1 |

Additionally, some CpGs in particular genes (FGFR1, HIF1A, BGN, CHAD, GLI3 and CD4) appear to be sensitive to changes in growth conditions (e.g., prolonged growth as a monolayer), while some (CHAD, ANXA6, BGN, HIF1A and PRELP) are sensitive to induction with growth factors.

Figure 2:
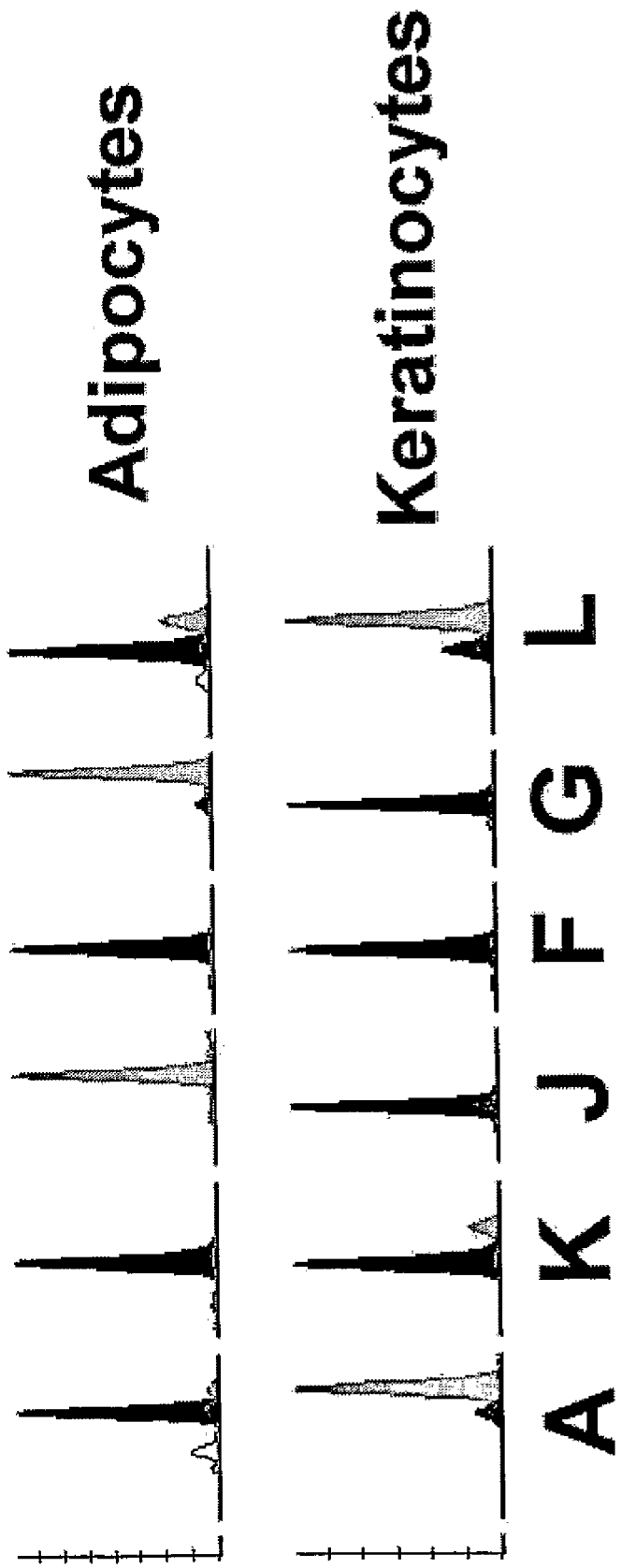
FIG. 2. Shows methylation profiles of six genes (A to F) from two cell types as generated by an MS-SNuPE method. Letters are as in FIG. 1.

The above regions therefore represent epigenetically sensitive markers that are then capable of distinguishing at least one cell type from any other cell types which display consistent methylation patterns within that region. In some cases, the methylation phenotypes were confirmed with a single base extension method (FIG. 2, see below). The finding of these methylation markers is a substantial advancement relative to the previous methods to characterise these cell types, as epitomised by the uncertain value of traditionally prototypical expression markers for chondrogenesis and osteogenesis (Kolettas et al., J Cell Sci 108:1991-9, 1995; Winter et al., Arthritis Rheum 48:418-29, 2003; Dell'Accio et al., Arthritis Rheum 44:1608-19, 2001; Benz et al., Biochem Biophys Res Commun 293:284-92, 2002).

FIG. 2 shows the distinctive methylation profiles of adipocytes and keratinocytes within six different genes (labelled as A, K, J, F, G and L). The profiles were generated using the MS-SNuPE method. The peak areas reflect the relative incorporation of C's (blue peaks) or T's (green peaks) onto an extension primer targeting a single CpG site in each gene. The ratio of the pairs of peaks (blue or green) at each site therefore corresponds to the relative methylation rate (methylated or unmethylated, respectively) of the targeted C in the genomic DNA of that sample. These ratios are characteristic and reproducible for many independent samples of these cell types. On a purely qualitative level, four of the markers (A, J, G and L) clearly distinguish adipocytes from keratinocytes, and in some cases the differential methylation between the two cell types reaches nearly 100%. The known ratio of these markers also allows one to calculate the quantity of each cell type within a heterogeneous mixture.

Completely resolving multiple unknown cell types within a batch will require between $N-1$ and $\log_2 N$ perfectly discriminative markers (where N is the number of cell types in the batch)—the number depends on how much the information carried in the markers overlaps with that of the other markers. In some cases, the markers are, in fact, useful to discriminate multiple subgroupings of cell types (as illustrated below); this tends to reduce the required number of markers needed. On the other hand, more markers may be required to compensate for those markers showing some biological variation.

As an example, the inventors can construct a dichotomous key, which incrementally splits the possible cell types according to a series of logical division points. For example, a possible first step would be to (logically) separate keratinocytes and melanocytes from osteoblasts, MSCs, fibroblasts, adipocytes and chondrocytes based on the methylation differences in COL6A3 and GDF5. Fibroblasts and adipocytes can be split from the latter grouping by differences in COL3A1. Fibroblasts are distinguished from adipocytes by differences in BGN and CAV1. Osteoblasts and MSCs can be separated from chondrocytes by differences in FMOD, KRT8 and SPP1. Osteoblasts are distinguished from MSCs by ANXA6. Finally, keratinocytes and melanocytes can be separated by methylation differences in CAV1 and ANXA6. In this case, a panel of eight markers resolves all the cell types; some of the markers operate at multiple division points (e.g., CAV1 and ANXA6), but some marker multiplicity is included to compensate for groupings that might be difficult to separate. Regardless of the logical structure of the key, this panel of markers would probably be tested simultaneously, allowing the calculation of the relative proportions of mixed cell types within a batch. It may be possible to use only a subset of markers (e.g., COL6A3, ANXA6, COL3A1, CAV1 and SPP1) to distinguish all the cell types, albeit with a lesser degree of confidence. Using a larger collection of markers not only reduces the uncertainty (due to measurement error and biological variation) but also makes the dichotomous key more likely to extend to other cell types.

Typically a combination of markers would generally be necessary to calculate mixtures of cells (as described above employing a system of multiple equations) and to resolve whether marker measurements were due to cells with intermediate methylation levels or due to mixtures of cell types with absolute methylation levels (i.e., 0% or 100%). Such an approach would employ marker profiles describing the methylation level at particular CpGs of each marker for a particular cell type. For example, the approximate methylation profile for melanocytes would be CHAD, COL6A3, GDF5, CAV1, ANXA6, ACVRL1, PRELP, FMOD, CNTN1, HIF1A, SPP1, COL3A1, GLI3, KRT8=1.0; COL2A1=0.9; PTHR1=0.5; FGFR1=0.3 and BGN=0.

These markers are also likely to be useful in determining the potency of individual batches of cells to effect a particular medical outcome, such as a successful Autologous Chondrocyte Transplantation. Class prediction methods employing learning algorithms (such as a Support Vector Machine) are particularly useful in cases where the exact the physiological or biochemical relationship to medical outcome are not known. However, it is difficult to predict a priori how many markers would be the optimal number for any specific usage; this number arises from the outcome of complex statistical algorithms and subsequent feature selection to distinguish, e.g., "therapeutic" from "non-therapeutic" batches of cells for that specific application. In one example of using methylation markers to distinguish between various types of tumours, 2 CpGs gave an 85% accuracy in class prediction, but 60 CpGs increased the accuracy to 94%. In another case, the optimal number was 5 CpGs, giving an accuracy of 94% (Adorjan P et al., Nucleic Acids Res 2002 30:e21, 2002). Given the uncertainty of predicting beforehand exactly what characteristics are most indicative of a "therapeutically successful" batch of cells and which genes/CpGs will prove most discriminatory, a good estimate would be between 5 and 25 markers as class predictors for any particular application.

Although the candidate genes in the inventors initial screening were generally selected based on literature, there is, as yet, no method to predict a priori how, when or where methylation changes will occur; finding them is overwhelmingly an empirical exercise, requiring intensive and laborious research. The connection between protein or gene expression and methylation patterns is, at best, asymmetric; increased methylation often correlates with decreased expression, but the reverse (i.e., changes in gene expression mean changes in methylation) is not necessarily, or even generally, true. The biological rules that dictate the interplay between methylation and gene expression are not known in spite of various approaches to deduce them (Jones, Trends Genet 15:34-7, 1999; Feltus et al., Proc Natl Acad Sci USA 100:12253-8, 2003; Millar et al., J Biol Chem 275:24893-9, 2000). The interactions between methylation and gene regulation may prove to be as complex as that already known for the transcriptional apparatus since factors such as CpG islands, enhancers, silencers, various non-coding RNAs and repetitive or parasitic insertion elements have been implicated (Bestor and Tycko, Nat Genet 12:363-7, 1996; Hejnar et al., Proc Natl Acad Sci USA 98:565-9, 2001; Mutskov et al., Genes Dev 16:1540-54, 2002; Wolffe and Matzke, Science 286:481-

6, 1999; Antequera, Cell Mol Life Sci 60:1647-58, 2000motiftr03; Gidekel and Bergman, J Biol Chem 277:34521-30, 2002; Grewal and Moazed, Science 301:798-802, 2003; Bird, Genes and Dev 16:6-21, 2002).

Conversely, changes in methylation are strongly correlated with altered gene expression. There are a number of examples wherein methylation changes either cause decreased gene expression themselves or else they 'lock in' regulatory patterns that are caused by other factors (Erlich, J Cellular Chem 88:899-910, 2003). In the inventive research, altered methylation patterns were found in cell types for which no parallel gene expression data is known. Furthermore, in many cases, methylation analysis may be a superior discovery method compared to either RNA or protein expression analysis for reasons cited above (e.g., sensitivity, robustness, both quantitative and qualitative changes, etc.). Subtle changes in gene expression may be lost or overlooked in large scale expression analysis, but become apparent by a more focussed approach once altered methylation patterns have been detected. In various instances, the behaviour of the corresponding mRNAs and proteins may correlate with or be primed by epigenetic modifications in such way that they are or are not expressed in concurrence with the methylation state. In these instances the protein synthesis and RNA expression patterns are claimed in their ability to provide an indication of the cell type and status.

The initial identification of variably methylated sites is not trivial. At this point, possibly a few hundred tissue- or stage-specific methylation states are known (out of approximately 30,000 human genes), and most are connected to early development, rather than to adult tissue. The inventors encompassed approximately 150 genes and extensive methylation analysis by bisulfite sequencing yielded only 25 genes in which variable methylation concurred with different cell types. Similar results were obtained from a herculean effort by the Human Epigenome Project (Rakyan et al., PLoS Biol 2:e405, 2004), covering 90 genes in the MHC region, in which only about 10% of the amplicons showed variable methylation between different tissues (approximately the same rate as in our study). This is not unexpected since each amplicon may cover only 200-500 bases of a potential regulatory several Kb.

On the other hand, once variable methylation is uncovered for a human gene in one tissue, it is likely to be a useful marker for other tissues, as demonstrated by the patterns shown in FIG. 1. Many of the markers are also stage specific since they distinguish mesenchymal stem cells from their descendants comprising various cell types. Some of the CpGs in these regions are also sensitive to changes in the cell state, such as multiple passages in monolayer culture or maturation from pre-adipocytes to adipocytes.

Furthermore, neighbouring regions to those defined by SEQ ID NOs 76 to 153 are also likely to show differential methylation, since, in some cases, the variably methylated region extends to the end, and possibly beyond, the amplicons comprising the named sequences. Due to the phenomena of co-methylation and "spreading", discriminatory CpGs are likely to be found in regions adjacent to those the inventors have revealed here. For this reason, the present invention also encompasses all or contiguous differentially methylated regions associated with the gene(s) as part of the invention.

Example 2

The inventors showed that six different cell types can be unambiguously classified based on their individual methylation patterns. Furthermore, the methylation levels at four discriminatory cytosines are sufficient to identify all six cell types, providing a specific cell-type "barcode".

The inventors included adult fibroblasts (stroma), adipocytes (fat), chondrocytes (cartilage) and mesenchymal stem cells (MSCs), all derived from the mesoderm, as well as the ectoderm-derived skin cell types keratinocytes and melanocytes. With exception to MSCs, where only one donor was used, three independent samples of each cell type were tested. For detection of methylation differences in these cell types, approximately 150 genes were selected. While a few genes were picked due to specific expression in adipocytes or MSCs, most genes were chosen according to their reported impact on chondrocyte maturation. For each candidate gene, two electronic PCR products were designed to target CpG islands in the proximity of the transcriptional start site. Due to low complexity of bisulphite-converted DNA and the requirement to avoid CpG dinucleotides overlapping the primer binding site, primer pairs were successfully generated for only 250 amplicons.

Human primary cells were purchased from Cascade Biologics (Mansfield, United Kingdom), Cell Applications Inc. (San Diego, Calif., United States), Cambrex Bio Science (Verviers, Belgium) or were a gift from TransTissue GmbH (Berlin, Germany). Samples from three donors were used for each cell type, with the exception of mesenchymal stem cells (MSCs), where only one sample was used. Primary cells were cultured according to the supplier's recommendations. Maturation of adipocytes was achieved by following the supplier's protocol.

DNA was prepared using the DNeasy tissue kit (Qiagen, Hilden, Germany). RNA was isolated using Trizol (Invitrogen Inc., Carlsbad, Calif., United States) following the supplier's recommendations. For RNA isolation from cartilage tissue, 10 mg were homogenised and incubated with 133 µl Brom-Chlor-Propan (Sigma-Aldrich, Seelze, Germany). Subsequently, a DNeasy minikit (Qiagen) was used according to manufacturer's recommendations. Potential DNA contaminations were eliminated by treating 1 µg of total RNA with 1 U DNase I (Invitrogen Inc., Carlsbad, Calif., United States) according to manufacturers recommendation. The reaction was terminated by adding 1 µl of a 25 mM EDTA solution and incubation at 65° C. for 10 min.

Sodium bisulphite treatment of genomic DNA was performed according to Olek A. et al., 1996, with minor modifications. Since methylated cytosines have the same base-pairing characteristics as unmethylated cytosines, the DNA is first chemically modified to distinguish between the two species. Purified genomic DNA was treated with sodium bisulfite, resulting in the conversion of unmethylated cytosine to uracil. In a subsequent PCR uracil is, in turn, replicated as thymine. However, methylated cytosines are protected from conversion and remain as cytosines throughout amplification. Thus, detection of a C in sequencing reaction or MS-SNuPE analysis reflects methylation at that site whereas detection of a T reflects no methylation. PCRs were performed on MJ Research thermocyclers (Waltham, Mass., United States) in a final volume of 25 µl containing 1×PCR Buffer, 1 U Taq DNA polymerase (Qiagen, Hilden, Germany), 200 µM dNTPs, 12.5 pmol each of forward and reverse primers, and 7 ng of bisulphite-treated genomic DNA. The amplification conditions were 95° C. for 15 min followed by 40 cycles of 95° C. for 1 min., 55° C. for 45 sec and 72° C. for 1 min. and a final extension step of 10 min. at 72° C. PCR products were purified using ExoSAP-IT (USB Corp., Cleveland, Ohio, United States) and sequenced applying the PCR primers and the ABI Big Dye Terminator v1.1 cycle sequencing chemistry (Applied Biosystems, Foster City, Calif., United States) followed by capillary electrophoresis on an ABI 3100 genetic analyser. Trace files were interpreted using ESME software, which performs quality control, normalizes sequence traces, corrects for incomplete bisulphite conversion and allows for quantification of methylation signals (Song et al., Proc Natl Acad Sci USA 102: 3336-3341, 2005).

To assess the methylation rate of individual CpGs, the inventors performed MS-SNuPE using the ABI Prism Snapshot multiplex kit (Applied Biosystems, Foster City, Calif., United States). The substrates were PCR products as produced from bisulphite converted genomic DNA. The assay utilizes internal primer(s) annealing immediately 3' of the nucleotide to be assayed. In the reaction, in the presence of labelled dideoxy NTP's, the primer is extended by exactly one nucleotide. Analysis of the elongated primer was performed by capillary electrophoresis using the ABI 3100 "Genetic Analyser" and "GeneMapper" software (v3.5). Extension Primer Sequences:

```
COL6A3: AACTCAAAAAACATCTCCCAAC;

COL3A1: AAAAACTAAAACAAAAAATAAC;

CAV1: AAATTAAAAATCTTCATTTCTTATTTC;

FMOD: TAATTATTCTAAAAATACACATACTTCATAC.
```

For first strand cDNA synthesis, the inventors used 200 ng DNase I treated RNA following the RevertAid reverse transcriptase kit protocol (Fermentas, St. Leon-Rot, Germany). First strand cDNA was directly used for PCR amplification. To assess expression levels of selected genes (semi-) quantitatively, we performed RT-PCR analysis according to Marone et al. 2001. Primers had a melting temperature of approx. 60° C. and were positioned to span two conserved exons at the 5' end of the transcripts. Amplification of GDF5, FMOD and COL3A1 was performed in a total volume of 20 µl containing 1 µl cDNA, 1× reaction buffer, 0.5 units HotStarTaq DNA polymerase (Qiagen, Hilden, Germany), 3 µM $MgCl_2$, 0.4 µM dNTP's, 0.5 µM of the specific primer pair, 0.125 µM aldolase (housekeeping control) specific primers. Amplification of COL6A3 contained 0.0625 µM aldolase specific primers and was otherwise identical. Amplification was performed at 95° C. for 15 min, followed by 32 amplification cycles for genes GDF5, FMOD and COL3A1 and 30 cycles for COL6A3 at 95° C. for 1 min, 55° C. for 45 sec and at 72° C. for 1 min. Amplificates were separated gelelectrophoretically in the presence of ethidium bromide and quantified with the "Gene Tools" program on a Syngene Bio Imaging System (Cambridge, United Kingdom). Target gene specific signals were normalized against the aldolase transcript.

In an initial screen, PCR products were sequenced for one sample per cell type in order to identify potentially differentially methylated gene regions. Due to the difficulties to design specific and reliable PCR primers for bisulphited DNA, approximately 100 electronic PCR products of the initial 250 were removed from the screen, either because they failed to produce a specific fragment in more than two of the six cell types or they did not produce a reliable sequence trace. For the remaining 150 amplicons, three types of methylation results were observed: (i) 90 amplicons did not demonstrate cell type-specific differential methylation, i.e., all tested samples showed the same methylation status. Of these, 72 sequenced gene regions showed no or very low methylation, while 18 sequences showed high methylation rates equally in all cell types. (ii) 35 amplicons showed intermediate levels of methylation in all cell types. Accordingly, observed differences were only moderate or detectable only at individual CpGs. (iii) 25 amplicons were selected as potential cell type-specific, large scale differentially methylated regions (CDMs). Bisulphite sequencing was performed for these amplicons on all available samples. In this analysis another four amplicons failed to show robust PCR products or sequencing results.

For the remaining 21 gene regions the inventors calculated the pairwise Euclidean distances between all cell samples applying the methylation information for sequenced CpGs. Since the number of comparable CpG measurements differed from pair to pair, they normalised these distances to the number of available CpGs. Thus, intervals in the tree directly translate into Euclidean distance per CpG. As shown in FIG. 2, the samples cluster into the five adult cell types, indicating that the average distance between the same cell type obtained from different donors is less than the distance between different cell types. For the adult cells, the farthest distance is observed between the ectodermally-derived cell types (keratinocytes and melanocytes), and the mesoderm-derived cell types. Note therefore, that the observed Eucledian distances of the differentially methylated regions reflect the developmental intervals of different cell types. Also, distances appear to be large enough for unambiguous differentiation between melanocytes and keratinocytes. Within the mesoderm-derived cell types, chondrocytes are easily segregated from fibroblasts and adipocytes, with large Euclidean distances between the branch points. The single MSC sample straddles the chondrocyte cluster and the branch leading to adipocytes and fibroblasts. According to this analysis, it is most difficult to distinguish fibroblast from adipocyte samples, which lie on the same main branch in the phylogenic tree. Fibroblasts B and C, and adipocytes A, B and C clearly fall into different categories, but the position of fibroblast sample A is somewhat ambiguous. The observed difficulty to differentiate these to cell types may be due to the original selection of candidate regions, which specifically targeted chondrocyte markers. According to this cluster analysis, 15 of the 16 samples can be correctly assigned to a cell type. Together, it appears that the measured methylation profiles are principally capable of distinguishing all analysed cell types.

Faced with the limitation of only three available samples per cell type, an exhaustive validation of the statistical significance of the discriminating regions was not possible. However, potent discriminators were selected to serve as tool for "cell typing" based on the following phenomenological and biological criteria: (i) Since it has been reported that differentially methylated genes were mostly found to be in a bimodal state, i.e. either strongly methylated or unmethylated (Lorincz et al. Mol. Cell Biol 22: 7572; 2002) the difference of the methylation rate between any two cell types as averaged throughout all CpG's of the analysed region were set to exceed 60%. (ii) Genes were regarded as potent discriminators, when a low variation among all tested donors of a particular cell type was demonstrated. (iii) Gene regions were primarily selected, when methylation occurred not only at individual CpGs, but appeared to span a wide-range of CpG methylation throughout the analysed region, a phenomenon named co-methylation. While each CpG in such cluster is not a statistically independent variable, the repetitive occurrence of various uniformly methylated CpGs within a short stretch of DNA in the CDMs suggests a biological significance, minimizing the chance of this observation to be a stochastic event. In FIG. 2, out of 21 cell type specifically methylated regions, 9 selected separators are shown. Some of the displayed gene regions were found as large blocks of consecutive CpGs, which are either highly methylated (95-100%) or effectively unmethylated (0-15%) in a given cell type. Additionally, there are gene regions, which are clearly distinctive between different groups, while not displaying strictly bimodal methylation patterns.

As was expected from the phylogenic tree, the clearest distinction was achieved between the two ectoderm-derived cell types versus all the cell types originating from the mesoderm. The amplicons derived from the gene regions associated with COL6A3 and GDF-5 unambiguously segregate them from the mesoderm-derived tissues, being methylated in both keratinocytes and melanocytes, while they appear unmethylated in fibroblasts, chondrocytes and adipocytes. All kerantinocyte and melanocyte samples consistently showed 100% methylation while adipocytes and chondrocytes unmethylated. Fibroblasts showed less consistent data, i.e., CpGs were intermediately methylated or were rather variable in this cell type among donors. Four CpGs in Caveolin-1 (CAV-1) are distinctively methylated between melanocytes and keratinocytes, with nearly 100% methylation in melanocytes but are primarily unmethylated in keratinocytes. Together, CAV-1 and either COL6A3 or GDF-5 are sufficient to separate melanocytes and keratinocytes, segregating them from each other and from all other tested cell types. Both FMOD and HIF1A are unmethylated in chondrocytes, while methylated in all other cell types. FMOD in particular exhibits discriminatory CpGs, with 0% methylation in all chondrocyte samples and 100% methylation in melanocytes, keratinocytes, adipocytes and fibroblasts. HIF1A was similarly distinctive for all cell types except adipocytes, where some ambiguity was introduced by low quality of the respective sequence trace. However, both genes individually allow for a clear discrimination of chondrocytes versus all other tested cell types. In adipocytes and fibroblasts, Collagen 3A1 is unmethylated, while methylated in keratinocytes, melanocytes, chondrocytes and MSCs, distinguishing these groups from each other. Methylation rates in all samples, with the exception of fibroblasts, were bimodal and showed low donor variability. To further distinguish adipocytes from fibroblasts, BGN can be analysed. The analysed gene region is highly methylated in fibroblasts (ca. 80%) but remains unmethylated in adipocytes. For positive identification of mesenchymal stem cells, SPP1 can be used. Although this gene does not display the bimodal methylation pattern, it appears that differentiated cells are 100% methylated, while the analysed MSC sample is only 50-60% methylated at particular CpGs. The ANXA-6 gene shows significant methylation differences between keratinocytes, fibroblasts and chondrocytes, which are rather unmethylated compared to adipocytes and melanocytes. As such, it could be used as confirmation of the CAV-1 gene to verify the distinction of the ectoderm-derived from each other.

Methylation states of selected individual CpGs in nine highly discriminatory gene regions (FIG. 5) are summarized in Table 3, which shows the average methylation rate and standard deviation within each cell type. Surprising signal stability is observed in particular for highly methylated regions, such as for FMOD in adipocytes, fibroblasts and keratinocytes. The sequencing data show no trace of unmethylated cytosine at these CpGs. Regions that are predominantly unmethylated show somewhat higher variability, such as within COL6A3 in chondrocytes or ANXA6 in keratinocytes. The least stable are those regions that appear to be in an intermediate state of methylation, such as ANXA6 in fibroblasts and CAV-1 in chondrocytes.

In order to adapt the observed markers to a platform suitable as a convenient cell-typing assay (and as a technical verification of the sequencing data), the inventors applied MS-SNuPE (Bird et al., Genes Dev 16: 6-21, 2002). Conventional SNuPE has previously been used for the precise detection of single nucleotide polymorphisms (SNPs) (Gonzalgo and Jones, NAR 25(12): 2529, 1997; Szabo and Mann, Genes Dev 9: 3097, 1996). Here, SNPs generated by bisulphite treatment distinguish between methylated cytosine (remaining as cytosine) and unmethylated cytosine (converted to thymine).

The sequencing results suggested that a methylation marker panel consisting of CpGs associated with genes CAV1, COL3A1, COL6A3 and FMOD can provide unique fingerprints for all analysed cell types. For each of these gene regions, individual CpGs (as shown in Table 3) were selected for MS-SNuPE based on the ability to design MS-SNuPE primers at these positions, their discriminatory power and the signal stability among samples of the same cell type.

The results from the MS-SNuPE assays closely paralleled that of the bisulfite sequencing. In most cases the signal generated at the respective CpGs showed either 0% or 100% methylation for the cell sample with no detectable peak for the alternative extension product.

From this data, the inventors can construct binary barcodes—with methylated CpG coding as 1 and unmethylated CpG coding as 0—for CpGs in the gene regions of COL6A3/COL3A1/CAV1/FMOD, respectively. As shown in the upper panel of FIG. 6, MS-SNuPE analysis of melanocytes revealed that the targeted CpG for all four genes were invariably methylated, with no detectable peaks representing unmethylated CpG at the analysed positions. This result translates into a melanocyte-specific barcode of "1111". Analysis of keratinocytes shows that three out of the four analysed CpGs are fully methylated, while the targeted CpG in CAV-1 was found to be unmethylated. Therefore, the keratinocyte-specific barcode for the measured CpGs is "1101". Thus, the selected CpG in the CAV-1 gene provides for the distinction of keratinocytes from melanocytes. Note that, while no signal for the unmethylated CpG is detected in either FMOD or COL3A1, a minor peak representing 2-3% of the total signal intensity for the COL6A3 gene appears to be unmethylated. In adipocytes, the analysis shows that the CpGs derived from CAV-1 and FMOD are entirely methylated, while COL6A3 and COL3A1 are unmethylated, translating in the barcode "0011". For COL3A1, a peak representing ca. 1-2% of the total signal intensity indicates a minor portion of methylated signal to be present. Analysis of chondrocytes reveals unmethylated CpGs for FMOD and COL6A3, and a fully methylated CpG in COL3A1. The CAV-1 gene shows strong signals for methylated as well as unmethylated CpG; this CpG is heterogeneously methylated at this position and can not cannot be used as an absolute indicator for this cell type. A chondrocyte-specific binary barcode would therefore be undetermined at this position and translates into "01X0". However, the CpG measured for FMOD is uniquely unmethylated in chondrocytes and methylated in all other cell types, allowing positive identification within the barcode. MSCs also produce a unique pattern with the analysed CpG from COL6A being unmethylated while all other CpGs are methylated, thus translating into the barcode "0111". Finally, fibroblasts display the specific barcode of "0001".

For a representative analysis of the gene expression in the differentially methylated genes, we chose regions with consistent and prominent methylation differences throughout long stretches of dense CpG regions. Collagen 6A3, GDF-5, Collagen 3A1 and FMOD fulfil these criteria and also appear to be powerful discriminators between different types of cells (FMOD) or different lineages (COL6A3, GDF-5). The bisulphite sequenced gene regions for GDF-5 and FMOD both map to the second exon of their respective genes, while the analysed region for COL6A3 aligns to its first intron adjacent to the 5' untranslated region. The amplicon for Collagen 3A1 maps to the promoter region, app. 1.8 kb upstream of the transcriptional start site of the gene and was included in this analysis due to its high methylation in keratinocytes and chondrocytes, and its low methylation in fibroblasts. For analysis we selected chondrocytes, fibroblasts and keratinocytes, representing both ectoderm- and mesoderm-derived cell types. For both FMOD and COL6A3, low methylation corresponds to expression and heavy methylation corresponds to little or no expression in all three cell types. For GDF5, heavy methylation again corresponds to no expression of the gene (in keratinocytes), while one of the two cell types with low methylation (chondrocytes) shows no expression. Finally, in COL3A1, methylation and expression are reciprocally related in fibroblasts and keratinocytes, but high expression accompanies heavy methylation in chondrocytes.

Example 3

The inventors furthermore showed that seven markers can be used to unambiguously classify chondrocytes from synovial fibroblasts. The following amplicons displayed a significant differential methylation pattern that allows for the discrimination between chondrocytes and synoviocytes FMOD (Fibromodulin)/AMP43 (SEQ ID No: 154)

Fibromodulin is a member of a family of small interstitial proteoglycans, containing a central region composed of leucine-rich repeats with 4 keratan sulfate chains flanked by disulfide-bonded terminal domains. It may participate in the assembly of the extracellular matrix as it interacts with type I and type II collagen fibrils and inhibits fibrillogenesis in vitro. It may also regulate TGF-beta activities by sequestering TGF-beta into the extracellular matrix.

AMP43 maps to the 2nd exon of the FMOD gene. The genomic sequence of AMP43 is shown in SEQ ID No: 154.

FGFR1 (Basic Fibroblast Growth Factor Receptor1)/AMP164 (SEQ ID No: 155)

The vertebrate fibroblast growth factor receptor family is highly conserved between members and throughout evolution. The FGFR1 gene is alternatively spliced generating multiple splice variants that are differentially expressed during embryo development and in the adult body.

The restricted expression patterns of FGFR1 isoforms, together with differential expression and binding of specific ligands, leads to activation of common FGFR1 signal transduction pathways, but may result in distinctively different biological responses as a result of differences in cellular context. FGFR1 isoforms are also present in the nucleus in complex with various fibroblast growth factors where they function to regulate transcription of target genes. Fibroblast growth factors are also important regulators of chondrocyte proliferation and differentiation.

AMP164 maps upstream of the 5'-UTR of the FGFR1 gene. The genomic sequence of AMP164 is shown in SEQ ID No: 155.

HIF1A (Hypoxia-Inducible Factor 1 Alpha)/AMP179 (SEQ ID No: 156)

HIF1A functions as a master transcriptional regulator of the adaptive response to hypoxia. Under hypoxic conditions it activates the transcription of over 40 genes, including erythropoietin, glucose transporters, glycolytic enzymes, vascular endothelial growth factors and other genes whose protein products increase oxygen delivery or facilitate metabolic adaptation to hypoxia. HIF1A plays an essential role in embryonic vascularization, tumor angiogenesis and pathophysiology of ischemic disease. Binds to core DNA sequence 5'-[AG] CGTG-3' within the hypoxia response element (HRE) of target gene promoters. Activation requires recruitment of transcriptional coactivators such as CREBPB and EP300. Activity is enhanced by interaction with both, NCOA1 or NCOA2. Interaction with redox regulatory protein APEX seems to activate CTAD and potentiates activation by NCOA1 and CREBBP.

HIF1A is a putative molecular component (oxygen sensor) which regulates oxygen homeostasis and stress responsive genes in articular chondrocytes.

AMP179 maps to the 1st exon of the HIF1A gene. The genomic sequence of AMP179 is shown in SEQ ID No: 156.

KRT8 (Keratin 8, Type II Cytoskeletal)/AMP308 (SEQ ID No: 157)

KRT8, a structural protein, is involved in the organization/biogenesis of the cytoskeleton. It heterotetramerizes with KRT18 (two type I and two type II keratins).

AMP308 maps near the transcriptional start site, targeting a region spanning 1st exon, 5'-UTR and promotor of the KRT8 gene. The genomic sequence of AMP308 is shown in SEQ ID No: 157

PKNOX2 (PBX/Knotted 1 Homeobox 2)/AMP522 (SEQ ID No: 158)

PKNOX2 is a member of the three-amino-acid loop extension (TALE) homeodomain proteins which are highly conserved transcription modulators. Cooperative function among PKNOX-related proteins seem to be critical for regulating transcription, and thus for cellular proliferation and differentiation.

PKNOX2 is a novel TALE-homeodomain protein and may interact with PBX proteins and plays a role in tissue-specific regulation of transcription. Unlike transcription factor PKNOX1, which is broadly expressed in many tissues, PKNOX2 shows a more restricted mRNA expression pattern.

AMP522 maps to the 1st intron (near the transcriptional start site) of the PKNOX2 gene. The genomic sequence of AMP522 is shown in SEQ ID No: 158.

C15orf27/AMP537 (SEQ ID No: 156)

Predicted protein; (Ota T. et al. (2004) Complete sequencing and characterization of 21, 243 full-length human cDNAs. Nat Genet. 36(1):40-45)

AMP537 maps to the 3rd intron of the C15orf27 gene. The genomic sequence of AMP537 is shown in SEQ ID No: 159.

ROPN1L (Ropporin 1-Like Protein/AKAP-Associated Sperm Protein)/AMP549 (SEQ ID No: 160)

The protein encoded by this gene is a sperm protein, which interacts with A-kinase anchoring protein, AKAP3, through the amphipathic helix region of AKAP3. Type II regulatory subunit of cAMP-dependent protein kinase (PKARII) also binds to this helix domain of AKAP3, which allows PKARII to be targeted to specific subcellular compartments. It is suggested that sperm contains several proteins that bind to AKAPs in a manner similar to PKARII, and this encoded protein may be one of them.

AMP549 maps to the 3rd intron of the ROPN1L gene. The genomic sequence of AMP549 is shown in SEQ ID No: 160.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08298762B2). An electronic copy of the "Sequence Listing" will also be available from the USPTO upon request and payment of the fee set forth in 37 CFR 1.19(b)(3).

The invention claimed is:

1. A method for determining the presence of a cell type in a biological sample, comprising the step of determining the expression level of HIF1A, whereby said expression level of HIF1A is indicative of the presence of said cell type in said biological sample.

2. The method according to claim 1, wherein the step of determining the expression level comprises determining the level of HIF1A mRNA and/or protein expression and/or performing an analysis of the level of an epigenetic marker of HIF1A.

3. The method according to claim 2, wherein the epigenetic marker of HIF1A is the methylation status of HIF1A.

4. The method according to claim 3, wherein said analysis of the methylation status comprises an analysis selected from promoter methylation, CpG island methylation, and/or analysis of at least one CpG in SEQ ID NO:156, or a sequence complementary to SEQ ID NO:156.

5. The method according to claim 3, wherein said analysis of the methylation status comprises at least one of the following methods: MSP, HeavyMethyl, MethyLight, and Ms-SNuPE.

6. The method according to claim 3, wherein said analysis of the methylation status comprises a chemical or enzymatic conversion of the DNA.

7. The method according to claim 6, wherein the converted DNA is subsequently amplified.

8. The method according to claim 2, further comprising a prediction of the quality and/or suitability of said cell type as a therapeutic, wherein the level of the epigenic marker of HIF1A is indicative of the quality and/or suitability of said cell type as a therapeutic.

9. The method according to claim 8, wherein the epigenetic marker of HIF1A is the methylation status of HIF1A.

10. The method according to claim 2, further comprising an estimation or prediction of the potency of said cell type in its use as a therapeutic for an individual or between different individuals.

11. The method according to claim 1, wherein said cell type is present in said biological sample in a cell population, cellular batch, a heterogeneous population of cells, a sub-population of cells, a tissue, an organ and/or a non-human organism.

12. The method according to claim 1, further comprising determining the identity, cellular status, composition, relative proportion, absolute amount and/or potency of said cell type in said biological sample, wherein the expression level of HIF1A is indicative of the identity, cell type, cellular status, composition, relative proportion, absolute amount and/or potency of said cell type.

13. The method according to claim 1, wherein one or any combination of the following cell types are analysed: keratinocytes, chondrocytes, osteoblasts, melanocytes, fibroblasts, adipocytes, or mesenchymal stem cells.

14. The method according to claim 1, further comprising detecting and monitoring the response to chemical and/or biological substances interacting with growth or differentiation programs of said cell type.

15. The method according to claim 1, wherein furthermore the expression level of at least one additional gene selected from the group consisting of C15orf27, COL3A1, CAV1, PRELP, SPP1, CHAD, ANXA6, KRTHB6, BGN, LTA, FGFR1, GDF5, PTHR1, BMP4, GLI3, COL2A1, IGF2, LPIN1, TDGF1, KRT8, CD4, CNTN1, COL6A3, FMOD, PKNOX2, ROPN1L, and ACVRL1 is determined.

16. The method, according to claim 15, wherein the additional gene is C15orf27.

17. A method for determining the presence of a cell type in a biological sample wherein said method comprises:
  a) contacting said biological sample with one or more probes selected from i)-iii):
    i) a nucleic acid molecule comprising a sequence of at least 18 bases in length of a segment of chemically pretreated genomic DNA derived from HIF1A, or a sequence complementary thereto;
    ii) an oligomer comprising at least a base sequence having a length of at least 9 nucleotides which is complementary, or hybridizes under moderately stringent conditions, to a nucleic acid molecule according to i), and
    iii a set of oligomers of ii); and
  b) determining the level of HIF1A mRNA and/or the level of an epigenetic marker of HIF1A in said biological sample, wherein the level of HIF1A mRNA and/or the level of the epigenetic marker of HIF1A in said biological sample is indicative of the presence of said cell type.

18. The method according to claim 17, wherein said cell type is present in said biological sample in a cell population, cellular batch, a heterogeneous population of cells, a sub-population of cells, a tissue, an organ and/or a non-human organism.

19. The method according to claim 17, further comprising determining the identity, cellular status, composition, relative proportion, absolute amount and/or potency of said cell type in said biological sample, wherein the level of HIF1A mRNA and/or the level of the epigenetic marker of HIF1A is indicative of the identity, cell type, cellular status, composition, relative proportion, absolute amount and/or potency of said cell type.

20. The method according to claim 17, wherein the epigenetic marker of HIF1A is the methylation status of HIF1A.

21. The method according to claim 17, wherein said one or more probes are contained in a kit.

22. A method for determining the presence of a chondrocyte cell in a biological sample derived from a human, comprising the step of determining the methylation status level of HIF1A, whereby unmethylated HIF1A is indicative of the presence of said chondrocyte cell.

* * * * *

UNITED STATES PATENT AND TRADEMARK OFFICE
CERTIFICATE OF CORRECTION

PATENT NO.      : 8,298,762 B2
APPLICATION NO. : 11/908392
DATED           : October 30, 2012
INVENTOR(S)     : Sven Olek et al.

Page 1 of 1

It is certified that error appears in the above-identified patent and that said Letters Patent is hereby corrected as shown below:

Column 20,

Line 60, "$M_1=ax_{1a}+bx_{1b}+...nx_1n$" should read --$M_1 = ax_{1a} + bx_{1b} +... nx_{1n}$--

Column 20,

Line 62, "$M_2=ax_{2a}+bx_{2b}+...nx_2n$" should read --$M_2 = ax_{2a} + bx_{2b} +... nx_{2n}$--

Column 24,

Line 20, "Gene J=" should read --Gene J=Col6A3--

Column 37,

Line 53, "gene regions (FIG. 5) are summarized" should read --gene regions are summarized--

Column 38,

Lines 26-27, "respectively. As shown in the upper panel of FIG. 6, MS-SNuPE analysis of melanocytes" should read --respectively. MS-uPE analysis of melanocytes--

Signed and Sealed this
Nineteenth Day of February, 2013

Teresa Stanek Rea
*Acting Director of the United States Patent and Trademark Office*